United States Patent
Wittekind et al.

(12) 
(10) Patent No.: US 6,333,186 B1
(45) Date of Patent: Dec. 25, 2001

(54) MODIFIED FORMS OF HEPATITIS C NS3 PROTEASE FOR FACILITATING INHIBITOR SCREENING AND STRUCTURAL STUDIES OF PROTEASE: INHIBITOR COMPLEXES

(75) Inventors: Michael Wittekind, Doylestown, PA (US); Steven Weinheimer, Northford, CT (US); Yaqun Zhang, Holland, PA (US); Valentina Goldfarb, Franklin Park, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/478,479

(22) Filed: Jan. 6, 2000

Related U.S. Application Data

(60) Provisional application No. 60/115,271, filed on Jan. 8, 1999.

(51) Int. Cl.[7] ............................. C12N 9/50; C12N 9/00; C12N 5/00; C07H 21/02
(52) U.S. Cl. ........................ 435/219; 435/183; 435/325; 546/23.1
(58) Field of Search ............................ 435/219, 235.1, 435/69.1; 530/350

(56) References Cited

U.S. PATENT DOCUMENTS

| | | |
|---|---|---|
| 5,371,017 | 12/1994 | Houghton et al. . |
| 5,585,258 | 12/1996 | Houghton et al. . |
| 5,597,691 | 1/1997 | Houghton et al. . |
| 5,712,145 | 1/1998 | Houghton et al. . |
| 5,739,002 | 4/1998 | DeFrancesco et al. . |
| 5,843,752 | 12/1998 | Dasmahapatra et al. . |

FOREIGN PATENT DOCUMENTS

| | | |
|---|---|---|
| WO 91/15575 | 10/1991 | (WO) . |
| WO 96/36702 | 11/1996 | (WO) . |
| WO 97/08304 | 3/1997 | (WO) . |
| WO 98/11134 | 3/1998 | (WO) . |
| WO 98/12308 | 3/1998 | (WO) . |

OTHER PUBLICATIONS

Love et al. (1996) Cell 87:331–342.
Kim et al. (1996) Cell 87:343–355.
Ingallinella et al. (1998) Biochemistry 37:8906–8914.
Yan et al. (1998) Protein Science 7:837–847.
Taremi et al. (1988) Protein Science7:2143–2149.
Keutmann et al. (1992) Molecular Endocrinology 6:904–912.
Bianchi et al. (1994) J. Mol. Biol. 236:649–659.
DeFrancesco et al. (1996) 35:13282–13287.
Choo et al. (1989) Science 244:359–362.
Kuo et al. (1989) Science 244:362–364.
Choo et al. (1991) Proc. Of Natl Acad. Of Sciences 88:2451–2455.
Grakoui et al. (1993) Journal of Virology 67:2832–2843.
Bartenschlager et al. (1993) Journal of Virology 67:3835–3844.
Hijikata et al. (1993) Proc. of the Natl Acad. of Sciences 90:10773–10777.
Tomei et al. (1993) Journal of Virology 67:4017–4026.
Bartenschlager et al. (1994) Journal of Virology 68:5045–5055.
Eckart et al. (1993) Biochem. and Biophys. Res. Commun. 192:399–406.
Lin et al. (1994) Journal of Virology 68:8147–8157.
Manabe et al. Virology 198:636–644.
Chambers et al. (1990) Proc. of the Natl. Acad. of Sciences 87:8898–8902.
Xu et al. (1997) Journal of Virology 71:5312–5322.
Overton et al. (1995) Journal of General Virology 76:3009–3019.
Bartenschlager et al. (1995) Journal of Virology 69:7519–7528.
Bouffard et al. (1995) Virology 209:52–59.
Tanji et al. (1995) Journal of Virology 69:1575–1581.
Lin et al. (1995) Proc. of Natl. Acad. of Sciences 92:7622–7626.
Satoh et al. (1995) Journal of Virology 69:4255–4260.
Tanji et al. (1994) Gene 145:215–219.
Failla et al. (1995) Journal of Virology 69:1769–1777.
Shoji et al. (1995) Hepatology 22:1648–1655.
Lin et al. (1995) Journal of Virology 69:4373–4380.
Tomei et al. (1995) Journal of General Virology 77:1065–1070.
Shimizu et al. (1996) Journal of Virology 70:127–132.
Lin et al. (1995) Proc. of the Natl. Acad. of Sciences 92:7622–7626.
Suzuki et al. (1995) Journal of Gen. Virology 76:3021–3029.
Hong et al. (1996) Journal of Virology 70:4261–4268.
Steinkuhler et al. (1996) Journal of Virology 70:6694–6700.
Inoue et al. (1998) Biochem. and Biophys. Res. Commun. 245:478–482.
Kunkel et al. (1996) Prc. Natl Acad. Sciences 82:488–492.
Taliani et al. (1996) Analytical Biochem. 240:60–67.
Pasquo et al. (1996) Folding and Design 3:433–441.
Jin et al. (1995) Archives of Biochem. and Biophys. 323:47–53.
Hijikata et al. (1993) Journal of Virology 67;4665–4675.

(List continued on next page.)

*Primary Examiner*—Deborah J. R. Clark
*Assistant Examiner*—Eleanor Sorbello
(74) *Attorney, Agent, or Firm*—Audrey F. Sher

(57) ABSTRACT

The present invention relates to modified Hepatitis C NS3 proteases and modified Hepatitis C NS4a-NS3 fusion proteases. These proteins are highly soluble and are useful for NMR spectroscopy, X-ray crystallography, and inhibitor screening. DNA constructs are also provided.

26 Claims, 18 Drawing Sheets

OTHER PUBLICATIONS

The Solution Structue of the N–terminal Protease Domain of the Hepatitis C Virus (HCV) NS3 Protein Provides New Insights into its Activation and Catalytic Mechanism, Barbato G., Cicero D.O., Nardi M.C., Steinkuhler C., Cortese R., DeFrancesco R., and Bazzo R. Abstract from the Frontiers of NMR in Molecular Biology VI Keystone Meeting, (1999) Breckenridge CO.

Choo, Q.L. et al, "Genetic Organization and diversity of the hepatitis C virus", Proc. Natl. Acad. Sci. U.S.A. (1991) 88: 2451–2455.*

De Francesco, et al. Method for reproducing in vitro the proteolytic activity of the N53 protease of hepatitis C virus (HCV), WO 95/22985, Aug. 31, 1995.*

Alberts, et al. "Molecular Biology of the Cell" Third Edition, p. 511, Garland Publishing, Inc. New York and London.*

Markland et al. (1997) Journal of Gen. Virology, 78:39–43.

Branden et al (1991)Introduction to Protein Structure, pp. 11–15.

* cited by examiner h = homogenate; s = supernatant

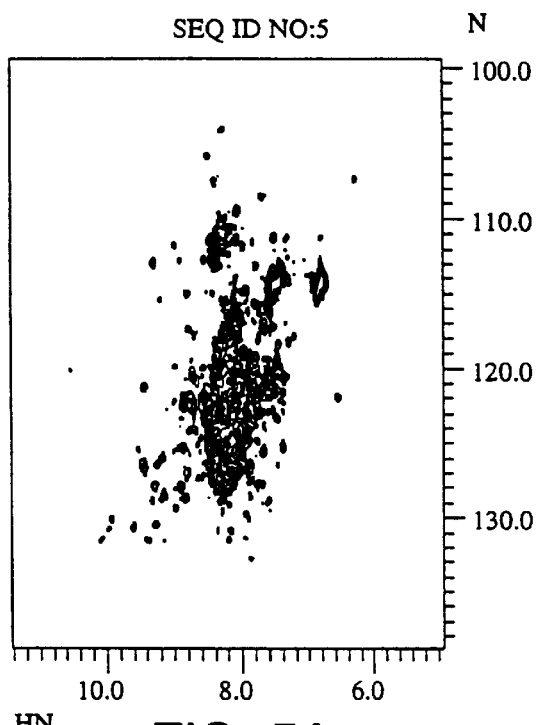
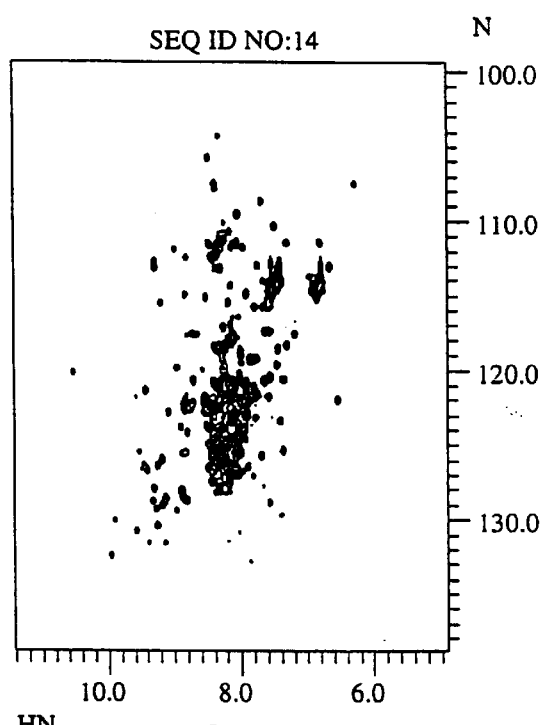
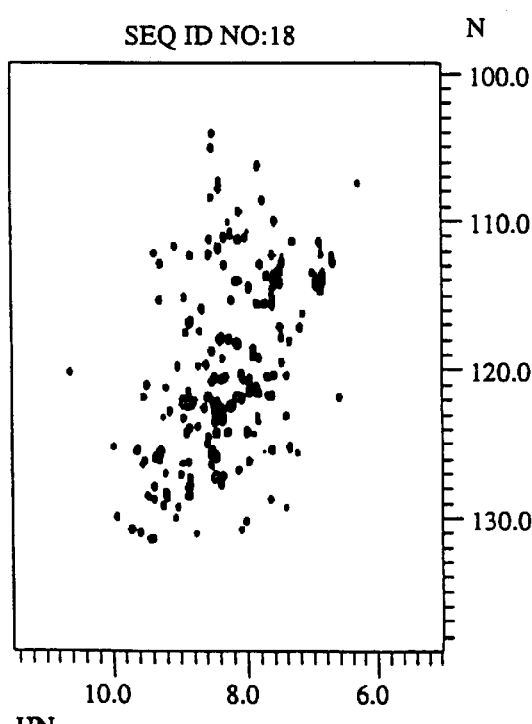
FIG. 5A
FIG. 5B
FIG. 5C

```
                          5                 10                20                30                40                50                60
Seq ID NO:1   ------------MAPITAYAQQTRGLLGCIITSLTGRDKNQVEGEVQIVSTAAQTFLATCINGVCWTVYHGAGTRTIA
Seq ID NO:3   MKKKGSVVIVGRIVL-NG--AYAQQTRGEEGCQETSQTGRDKNQVEGEVQIVSTAAQTFLATCINGVCWTVYHGAGTRTIA
Seq ID NO:12  MKKKGSVVIVGRIVL-NG--AYAQQTRGEEGCQETSQTGRDKNQVEGEVQIVSTAAQTFLATCINGVCWTVYHGAGTRTIA
Seq ID NO:14  MKKKGSVVIVGRINLSGDTAYAQQTRGEEGCQETSQTGRDKNQVEGEVQIVSTAAQTFLATCINGVCWTVYHGAGTRTIA
Seq ID NO:16  MKKKGSVVIVGRINLSGDTAYAQQTRGEEGCQETSQTGRDKNQVEGEVQIVSTAAQTFLATCINGVCWTVYHGAGTRTIA
Seq ID NO:18  MKKKGSVVIVGRINLSGDTAYAQQTRGEQGCQKTSHTGRDKNQVEGEVQIVSTATQTFLATSINGVLWTVYHGAGTRTIA
Seq ID NO:20  MKKKGSVVIVGRINLSGDTAYAQQTRGEQGCQKTSHTGRDKNQVEGEVQIVSTATQTFLATSINGVLWTVYHGAGTRTIA
Seq ID NO:22  MKKKGSVVIVGRINLSGDTAYAQQTRGEQGTQKTSHTGRDKNQVEGEVQIVSTATQTFLATSINGVLWTVYHGAGTRTIA
Seq ID NO:24  MKKKGSVVIVGRINLSGDTAYAQQTRGLLGCIITSLTGRDKNQVEGEVQIVSTAAQTFLATCINGVCWTVYHGAGTRTIA 70                80                90               100               110               120               130               140
Seq ID NO:1   SPKGPVIQMYTNVDKDLVGWPAPQGSRSLTPCTCGSSDLYLVTRHADVIPVRRRGDSRGSLLSPRPISYLKGSSGGPLLC
Seq ID NO:3   SPKGPVIQMYTNVDKDLVGWPAPQGSRSLTPCTCGSSDLYLVTRHADVIPVRRRGDSRGSLLSPRPISYLKGSSGGPLLC
Seq ID NO:12  SPKGPVIQMYTNVDKDLVGWPAPQGSRSLTPCTCGSSDLYLVTRHADVIPVRRRGDSRGSLLSPRPISYLKGSSGGPLLC
Seq ID NO:14  SPKGPVIQMYTNVDKDLVGWPAPQGSRSLTPCTCGSSDLYLVTRHADVIPVRRRGDSRGSLLSPRPISYLKGSSGGPLLC
Seq ID NO:16  SPKGPVIQMYTNVDKDLVGWQAPQGSRSLTPCTCGSSDLYLVTRHADVIPVRRRGDSRGSLLSPRPISYLKGSSGGPLLC
Seq ID NO:18  SPKGPVIQMYTNVDKDLVGWQAPQGSRSLTPCTCGSSDLYLVTRHADVIPVRRRGDSRGSLLSPRPISYLKGSSGGPLLC
Seq ID NO:20  SPKGPVTQMYTNVDKDLVGWQAPQGSRSLTPCTCGSSDLYLVTRHADVIPVRRRGDSRGSLLSPRPISYLKGSSGGPLLC
Seq ID NO:22  SPKGPVTQMYTNVDKDLVGWQAPQGSRSLTPCTCGSSDLYLVTRHADVIPVRRRGDSRGSLLSPRPISYLKGSSGGPLLC
Seq ID NO:24  SPKGPVTQMYTNVDKDLVGWPAPQGSRSLTPCTCGSSDLYLVTRHADVIPVRRRGDSRGSLLSPRPISYLKGSSGGPLLC 150               160               170               180
Seq ID NO:1   PAGHAVGIFRAAVCTRGVAKAVDFIPVESLETTMRS--
Seq ID NO:3   PAGHAVGIFRAAVCTRGVAKAVDFIPVESLETTMRSP-
Seq ID NO:12  PAGHAVGIFRAAVCTRGVAKAVDFIPVESLETTMRSP-
Seq ID NO:14  PAGHAVGIFRAAVCTRGVAKAVDFIPVESLETTMRSP-
Seq ID NO:16  PAGHAVGIFRAAVCTRGVAKAVDFIPVESLETTMRSP-
Seq ID NO:18  PAGHAVGIFRAAVCTRGVAKAVDFIPVESLETTMRSP-
Seq ID NO:20  PAGHAVGIFRAAVSTRGVAKAVDFIPVESLETTMRSP-
Seq ID NO:22  PAGHAVGIFRAAVSTRGVAKAVDFIPVESLETTMRSP-
Seq ID NO:24  PAGHAVGIFRAAVSTRGVAKAVDFIPVESLETTMRSP-
```

FIG. 6

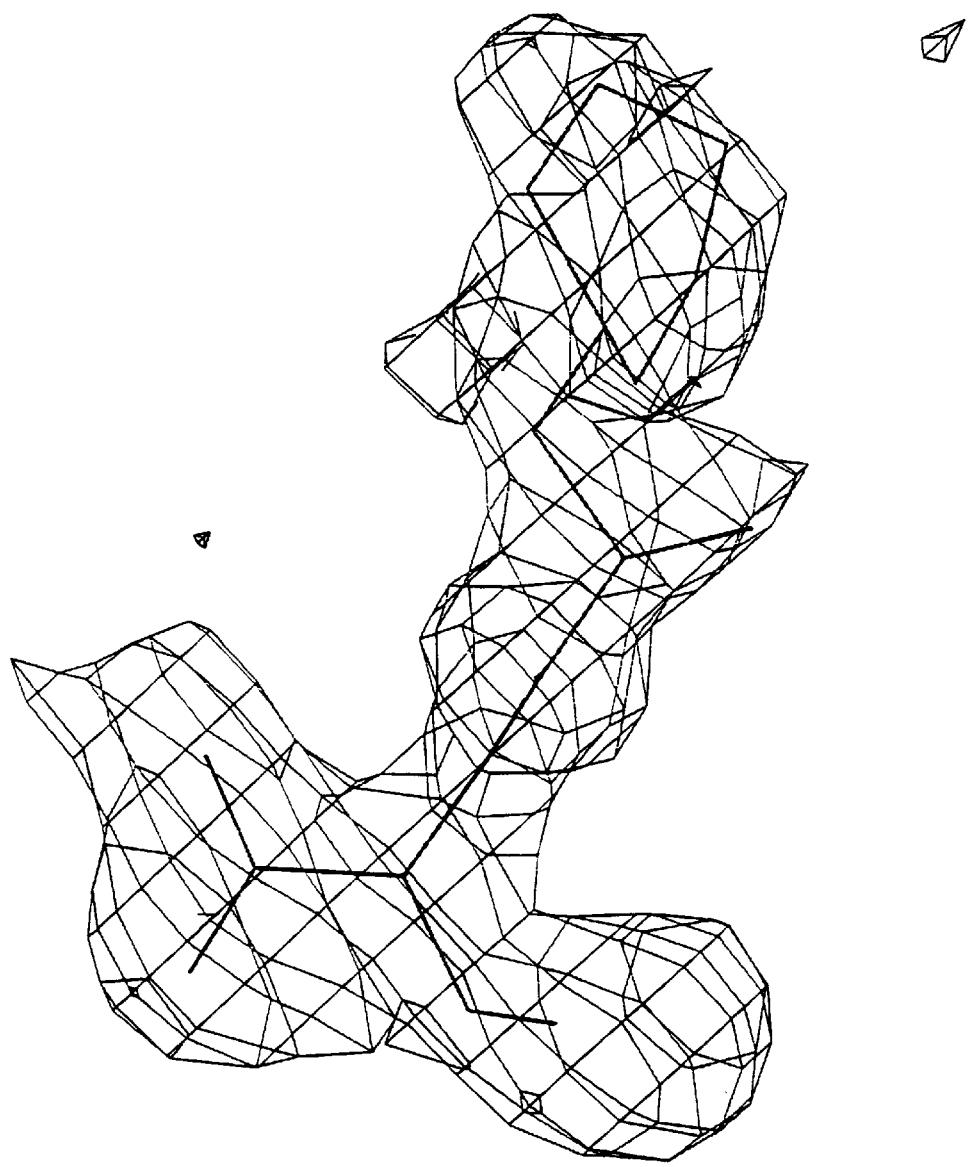
FIG. 8  ⊢−−⊣ 1.00 A

```
            M   A   P   I   T   A   Y       A   Q   Q       T   R   G   L       L   G   C       I   I   T
  1 ATGGCTCCGAT CACCGCTTA CGCTCAGCAG ACCCGTGGTC TGCTGGGTTG CATCATCACC
    TACCGAGGCT AGTGGCGAAT GCGAGTCGTC TGGGCACCAG ACGACCCAAC GTAGTAGTGG

S   L   T   G       R   D   K       N   Q   V       E   G   E   V       Q   I   V       S   T   A
 61 TCCCTGACCG GTCGTGACAA AAACCAGGTT GAAGGTGAAG TTCAGATCGT TTCCACCGCT
    AGGGACTGGC CAGCACTGTT TTTGGTCCAA CTTCCACTTC AAGTCTAGCA AAGGTGGCGA

A   Q   T       F   L   A   T       C   I   N       G   V   C       W   T   V   Y       H   G   A
121 GCTCAGACCT TCCTGGCTAC CTGCATCAAC GGTGTTTGCT GGACCGTTTA CCACGGTGCT
    CGAGTCTGGA AGGACCGATG GACGTAGTTG CCACAAACGA CCTGGCAAAT GGTGCCACGA

G   T   R   T       I   A   S       P   K   G       P   V   I   Q       M   Y   T       N   V   D
181 GGTACCCGTA CCATCGCTTC CCCGAAAGGT CCGGTTATCC AGATGTACAC CAACGTTGAC
    CCATGGGCAT GGTAGCGAAG GGGCTTTCCA GGCCAATAGG TCTACATGTG GTTGCAACTG

K   D   L   V       G   W   P       A   P   Q       G   S   R   S       L   T   P       C   T   C
241 AAAGACCTGG TTGGTTGGCC GGCTCCGCAG GGTTCCCGTT CCCTGACCCC GTGCACCTGC
    TTTCTGGACC AACCAACCGG CCGAGGCGTC CCAAGGGCAA GGGACTGGGG CACGTGGACG

G   S   S   D       L   Y   L       V   T   R       H   A   D   V       I   P   V       R   R   R
301 GGTTCCTCCG ACCTGTACCT GGTTACCCGT CACGCTGACG TTATCCCGGT TCGTCGTCGT
    CCAAGGAGGC TGGACATGGA CCAATGGGCA GTGCGACTGC AATAGGGCCA AGCAGCAGCA

G   D   S   R       G   S   L       L   S   P       R   P   I   S       Y   L   K       G   S   S
361 GGTGACTCCC GTGGTTCCCT GCTGTCCCCG CGTCCGATCT CCTACCTGAA AGGTTCCTCC
    CCACTGAGGG CACCAAGGGA CGACAGGGGC GCAGGCTAGA GGATGGACTT TCCAAGGAGG

G   G   P       L   C   P       A   G   H       A   V   G   I       F   R   A       A   V   C
421 GGTGGTCCGC TGCTGTGCCC GGCTGGTCAC GCTGTTGGTA TCTTCCGTGC TGCTGTTTGC
    CCACCAGGCG ACGACACGGG CCGACCAGTG CGACAACCAT AGAAGGCACG ACGACAAACG

T   R   G   V       A   K   A       V   D   F       I   P   V   E       S   L   E       T   T   M
481 ACCCGTGGTG TTGCTAAAGC TGTTGACTTC ATCCCGGTTG AATCCCTGGA AACCACCATG
    TGGGCACCAC AACGATTTCG ACAACTGAAG TAGGGCCAAC TTAGGGACCT TTGGTGGTAC

R   S   *
541 CGTTCCTGA
    GCAAGGACT                    FIG. 9
```

```
      M   K   K   K       G   S   V       V   I   V       G   R   I   V       L   N   G       A   Y   A
  1 ATGAAAAAAA AAGGTTCCGT TGTTATCGTC GGCCGTATAG TACTGAACGG TGCTTACGCT
    TACTTTTTTT TTCCAAGGCA ACAATAGCAG CCGGCATATC ATGACTTGCC ACGAATGCGA

Q   Q   T   R       G   L   L       G   C   I       I   T   S   L       T   G   R       D   K   N
 61 CAGCAGACTC GAGGTCTGCT GGGTTGCATC ATCACCTCCC TGACCGGTCG TGACAAAAAC
    GTCGTCTGAG CTCCAGACGA CCCAACGTAG TAGTGGAGGG ACTGGCCAGC ACTGTTTTTG

Q   V   E   G       E   V   Q       I   V   S       T   A   A   Q       T   F   L       A   T   C
121 CAGGTTGAAG GTGAAGTTCA GATCGTTTCC ACCGCTGCTC AGACCTTCCT GGCTACCTGC
    GTCCAACTTC CACTTCAAGT CTAGCAAAGG TGGCGACGAG TCTGGAAGGA CCGATGGACG

I   N   G   V       C   W   T       V   Y   H       G   A   G   T       R   T   I       A   S   P
181 ATCAACGGTG TTTGCTGGAC CGTTTACCAC GGTGCTGGTA CCCGTACCAT CGCTTCCCCG
    TAGTTGCCAC AAACGACCTG GCAAATGGTG CCACGACCAT GGGCATGGTA GCGAAGGGGC

K   G   P   V       I   Q   M       Y   T   N       V   D   K   D       L   V   G       W   P   A
241 AAAGGTCCGG TTATCCAGAT GTACACCAAC GTTGACAAAG ACCTGGTTGG TTGGCCGGCT
    TTTCCAGGCC AATAGGTCTA CATGTGGTTG CAACTGTTTC TGGACCAACC AACCGGCCGA

P   Q   G   S       R   S   L       T   P   C       T   C   G   S       S   D   L       Y   L   V
301 CCGCAGGGTT CCCGTTCCCT GACCCCGTGC ACCTGCGGTT CCTCCGACCT GTACCTGGTT
    GGCGTCCCAA GGGCAAGGGA CTGGGGCACG TGGACGCCAA GGAGGCTGGA CATGGACCAA

T   R   H   A       D   V   I       P   V   R       R   R   G   D       S   R   G       S   L   L
361 ACCCGTCACG CTGACGTTAT CCCCGGTTCGT CGTCGTGGTG ACTCCCGTGG TTCCCTGCTG
    TGGGCAGTGC GACTGCAATA GGGCCAAGCA GCAGCACCAC TGAGGGCACC AAGGGACGAC

S   P   R   P       I   S   Y       L   K   G       S   S   G       P   L   L       C   P   A
421 TCCCCGCGTC CGATCTCCTA CCTGAAAGGT TCCTCCGGTG GTCCGCTGCT GTGCCCGGCT
    AGGGGCGCAG GCTAGAGGAT GGACTTTCCA AGGAGGCCAC CAGGCGACGA CACGGGCCGA

G   H   A   V       G   I   F       R   A   A       V   C   T   R       G   V   A       K   A   V
481 GGTCACGCTG TTGGTATCTT CCGTGCTGCT GTTTGCACCC GTGGTGTTGC TAAAGCTGTT
    CCAGTGCGAC AACCATAGAA GGCACGACGA CAAACGTGGG CACCACAACG ATTTCGACAA

D   F   I   P       V   E   S       L   E   T       T   M   R   S       P   *
541 GACTTCATCC CGGTTGAATC CCTGGAAACC ACCATGCGTT CCCCGTGA
    CTGAAGTAGG GCCAACTTAG GGACCTTTGG TGGTACGCAA GGGGCACT
```

FIG. 10

|  |  |  |  |  |  |  | $L_{13}$ | $L_{14}$ |  |  | $I_{17}$ | $I_{18}$ |  |  | $L_{21}$ |  |
|---|---|---|---|---|---|---|---|---|---|---|---|---|---|---|---|---|
| Wild-type | (5) | Q | Q | T | R | G | L | L | G | C | I | I | T | S | L | T |
| Helix0-1 | (6) | . | . | . | . | . | E | E | . | . | Q | E | . | . | Q | . |
| Helix0-3 | (7) | . | . | . | . | . | E | E | . | . | Q | Q | . | . | E | . |
| Helix0-4 | (8) | . | . | . | . | . | N | Q | . | . | E | K | . | . | E | . |
| Helix0-7 | (9) | . | . | . | . | . | E | Q | . | . | Q | K | . | . | H | . |
| Helix0-8 | (10) | . | . | . | . | . | E | Q | . | . | D | E | . | . | E | . |
| Helix0-10 | (11) | . | . | . | . | . | E | E | . | . | E | Q | . | . | E | . |

FIG. 11

```
      M  K  K  K  G  S  V     V  I  V     G  R  I  V     L  N  G     A  Y  A
  1 ATGAAAAAAA AAGGATCCGT TGTTATCGTC GGCCGTATAG TACTGAACGG TGCTTACGCT
    TACTTTTTTT TTCCTAGGCA ACAATAGCAG CCGGCATATC ATGACTTGCC ACGAATGCGA

Q  Q  T  R     G  E  E     G  C  Q     E  T  S  Q     T  G  R     D  K  N
 61 CAGCAGACTC GAGGTGAGGA GGGTTGCCAA GAAACCTCCC AGACCGGTCG TGACAAAAAC
    GTCGTCTGAG CTCCACTCCT CCCAACGGTT CTTTGGAGGG TCTGGCCAGC ACTGTTTTG

Q  V  E  G     E  V  Q     I  V  S     T  A  A  Q     T  F  L     A  T  C
121 CAGGTTGAAG GTGAAGTTCA GATCGTTTCC ACCGCTGCTC AGACCTTCCT GGCTACCTGC
    GTCCAACTTC CACTTCAAGT CTAGCAAAGG TGGCGACGAG TCTGGAAGGA CCGATGGACG

I  N  G  V     C  W  T     V  Y  H     G  A  G  T     R  T  I     A  S  P
181 ATCAACGGTG TTTGCTGGAC CGTTTACCAC GGTGCTGGTA CCCGTACCAT CGCTTCCCCG
    TAGTTGCCAC AAACGACCTG GCAAATGGTG CCACGACCAT GGGCATGGTA GCGAAGGGGC

K  G  P  V     I  Q  M     Y  T  N     V  D  K  D     L  V  G     W  P  A
241 AAAGGTCCGG TTATCCAGAT GTACACCAAC GTTGACAAAG ACCTGGTTGG TTGGCCGGCT
    TTTCCAGGCC AATAGGTCTA CATGTGGTTG CAACTGTTTC TGGACCAACC AACCGGCCGA

P  Q  G  S     R  S  L     T  P  C     T  C  G  S     S  D  L     Y  L  V
301 CCGCAGGGTT CCCGTTCCCT GACCCCGTGC ACCTGCGGTT CCTCCGACCT GTACCTGGTT
    GGCGTCCCAA GGGCAAGGGA CTGGGGCACG TGGACGCCAA GGAGGCTGGA CATGGACCAA

T  R  H  A     D  V  I     P  V  R     R  R  G  D     S  R  G     S  L  L
361 ACCCGTCACG CTGACGTTAT CCCGGTTCGT CGTCGTGGTG ACTCCCGTGG TTCCCTGCTG
    TGGGCAGTGC GACTGCAATA GGGCCAAGCA GCAGCACCAC TGAGGGCACC AAGGGACGAC

S  P  R  P     I  S  Y     L  K  G     S  S  G  G     P  L  L     C  P  A
421 TCCCCGCGTC CGATCTCCTA CCTGAAAGGT TCCTCCGGTG GTCCGCTGCT GTGCCCGGCT
    AGGGGCGCAG GCTAGAGGAT GGACTTTCCA AGGAGGCCAC CAGGCGACGA CACGGGCCGA

G  H  A  V     G  I  F     R  A  A     V  C  T  R     G  V  A     K  A  V
481 GGTCACGCTG TTGGTATCTT CCGTGCTGCT GTTTGCACCC GTGGTGTTGC TAAAGCTGTT
    CCAGTGCGAC AACCATAGAA GGCACGACGA CAAACGTGGG CACCACAACG ATTTCGACAA

D  F  I  P     V  E  S     L  E  T     T  M  R  S     P  *
541 GACTTCATCC CGGTTGAATC CCTGGAAACC ACCATGCGTT CCCCGTGA
    CTGAAGTAGG GCCAACTTAG GGACCTTTGG TGGTACGCAA GGGGCACT
```

FIG. 12

```
      M   K   K   K      G   S   V      V   I   V      G   R   I   N      L   S   G      D   T   A
  1 ATGAAAAAAA AAGGATCCGT TGTTATCGTC GGCCGTATCA ACCTGTCCGG TGACACCGCT
    TACTTTTTTT TTCCTAGGCA ACAATAGCAG CCGGCATAGT TGGACAGGCC ACTGTGGCGA

Y   A   Q   Q      T   R   G      E   E   G      C   Q   E   T      S   Q   T      G   R   D
 61 TACGCTCAGC AGACTCGAGG TGAGGAGGGT TGCCAAGAAA CCTCCCAGAC CGGTCGTGAC
    ATGCGAGTCG TCTGAGCTCC ACTCCTCCCA ACGGTTCTTT GGAGGGTCTG GCCAGCACTG

K   N   Q   V      E   G   E      V   Q   I      V   S   T   A      A   Q   T      F   L   A
121 AAAAACCAGG TTGAAGGTGA AGTTCAGATC GTTTCCACCG CTGCTCAGAC CTTCCTGGCT
    TTTTTGGTCC AACTTCCACT TCAAGTCTAG CAAAGGTGGC GACGAGTCTG GAAGGACCGA

T   C   I   N      G   V   C      W   T   V      Y   H   G   A      G   T   R      T   I   A
181 ACCTGCATCA ACGGTGTTTG CTGGACCGTT TACCACGGTG CTGGTACCCG TACCATCGCT
    TGGACGTAGT TGCCACAAAC GACCTGGCAA ATGGTGCCAC GACCATGGGC ATGGTAGCGA

S   P   K   G      P   V   I      Q   M   Y      T   N   V   D      K   D   L      V   G   W
241 TCCCCGAAAG GTCCGGTTAT CCAGATGTAC ACCAACGTTG ACAAAGACCT GGTTGGTTGG
    AGGGGCTTTC CAGGCCAATA GGTCTACATG TGGTTGCAAC TGTTTCTGGA CCAACCAACC

P   A   P   Q      G   S   R      S   L   T      P   C   T   C      G   S   S      D   L   Y
301 CCGGCTCCGC AGGGTTCCCG TTCCCTGACC CCGTGCACCT GCGGTTCCTC CGACCTGTAC
    GGCCGAGGCG TCCCAAGGGC AAGGGACTGG GGCACGTGGA CGCCAAGGAG GCTGGACATG

L   V   T   R      H   A   D      V   I   P      V   R   R   R      G   D   S      R   G   S
361 CTGGTTACCC GTCACGCTGA CGTTATCCCG GTTCGTCGTC GTGGTGACTC CCGTGGTTCC
    GACCAATGGG CAGTGCGACT GCAATAGGGC CAAGCAGCAG CACCACTGAG GGCACCAAGG

L   L   S   P      R   P   I      S   Y   L      K   G   S   S      G   G   P      L   L   C
421 CTGCTGTCCC GCGTCCGATC TCCTACCTG AAAGGTTCCT CCGGTGGTCC GCTGCTGTGC
    GACGACAGGG CGCAGGCTA GAGGATGGAC TTTCCAAGGA GGCCACCAGG CGACGACACG

P   A   G   H      A   V   G      I   F   R      A   A   V   C      T   R   G      V   A   K
481 CCGGCTGGTC ACGCTGTTGG TATCTTCCGT GCTGCTGTTT GCACCCGTGG TGTTGCTAAA
    GGCCGACCAG TGCGACAACC ATAGAAGGCA CGACGACAAA CGTGGGCACC ACAACGATTT

A   V   D   F      I   P   V      E   S   L      E   T   T   M      R   S   P      *
541 GCTGTTGACT TCATCCCGGT TGAATCCCTG GAAACCACCA TGCGTTCCCC GTGA
    CGACAACTGA AGTAGGGCCA ACTTAGGGAC CTTTGGTGGT ACGCAAGGGG CACT
```

FIG. 13

```
              M   K   K   K   G   S   V       V   I   V       G   R   I   N       L   S   G       D   T   A
  1 ATGAAAAAAA AAGGATCCGT TGTTATCGTC GGCCGTATCA ACCTGTCCGG TGACACCGCT
    TACTTTTTTT TTCCTAGGCA ACAATAGCAG CCGGCATAGT TGGACAGGCC ACTGTGGCGA

Y   A   Q   Q       T   R   G       E   E   G       C   Q   E   T       S   Q   T       G   R   D
 61 TACGCTCAGC AGACTCGAGG TGAGGAGGGT TGCCAAGAAA CCTCCCAGAC CGGTCGTGAC
    ATGCGAGTCG TCTGAGCTCC ACTCCTCCCA ACGGTTCTTT GGAGGGTCTG GCCAGCACTG

K   N   Q   V       E   G   E       V   Q   I       V   S   T   A       T   Q   T       F   L   A
121 AAAAACCAGG TTGAAGGTGA AGTTCAGATC GTTTCCACCG CTACCCAGAC CTTCCTGGCT
    TTTTTGGTCC AACTTCCACT TCAAGTCTAG CAAAGGTGGC GATGGGTCTG GAAGGACCGA

T   C   I   N       G   V   C       W   T   V       Y   H   G   A       G   T   R       T   I   A
181 ACCTGCATCA ACGGTGTTTG CTGGACCGTT TACCACGGTG CTGGTACCCG TACCATCGCT
    TGGACGTAGT TGCCACAAAC GACCTGGCAA ATGGTGCCAC GACCATGGGC ATGGTAGCGA

S   P   K   G       P   V   T       Q   M   Y       T   N   V   D       K   D   L       V   G   W
241 TCCCCGAAAG GTCCGGTTAC CCAGATGTAC ACCAACGTTG ACAAAGACCT GGTTGGTTGG
    AGGGGCTTTC CAGGCCAATG GGTCTACATG TGGTTGCAAC TGTTTCTGGA CCAACCAACC

Q   A   P   Q       G   S   R       S   L   T       P   C   T   C       G   S   S       D   L   Y
301 CAGGCTCCGC AGGGTTCCCG TTCCCTGACC CCGTGCACCT GCGGTTCCTC CGACCTGTAC
    GTCCGAGGCG TCCCAAGGGC AAGGGACTGG GGCACGTGGA CGCCAAGGAG GCTGGACATG

L   V   T   R       H   A   D       V   I   P       V   R   R   R       G   D   S       R   G   S
361 CTGGTTACCC GTCACGCTGA CGTTATCCCG GTTCGTCGTC GTGGTGACTC CCGTGGTTCC
    GACCAATGGG CAGTGCGACT GCAATAGGGC CAAGCAGCAG CACCACTGAG GGCACCAAGG

L   L   S   P       R   P   I       S   Y   L       K   G   S   S       G   G   P       L   L   C
421 CTGCTGTCCC GCGTCCGAT CTCCTACCTG AAAGGTTCCT CCGGTGGTCC GCTGCTGTGC
    GACGACAGGG CGCAGGCTA GAGGATGGAC TTTCCAAGGA GGCCACCAGG CGACGACACG

P   A   G   H       A   V   G       I   F   R       A   A   V   C       T   R   G       V   A   K
481 CCGGCTGGTC ACGCTGTTGG TATCTTCCGT GCTGCTGTTT GCACCCGTGG TGTTGCTAAA
    GGCCGACCAG TGCGACAACC ATAGAAGGCA CGACGACAAA CGTGGGCACC ACAACGATTT

A   V   D   F       I   P   V       E   S   L       E   T   T   M       R   S   P       *
541 GCTGTTGACT TCATCCCGGT TGAATCCCTG GAAACCACCA TGCGTTCCCC GTGA
    CGACAACTGA AGTAGGGCCA ACTTAGGGAC CTTTGGTGGT ACGCAAGGGG CACT
```

FIG. 14

```
        M   K   K   K       G   S   V       V   I   V       G   R   I   N       L   S   G       D   T   A
  1  ATGAAAAAAA AAGGATCCGT TGTTATCGTC GGCCGTATCA ACCTGTCCGG TGACACCGCT
     TACTTTTTTT TTCCTAGGCA ACAATAGCAG CCGGCATAGT TGGACAGGCC ACTGTGGCGA

Y   A   Q   Q       T   R   G       E   E   G       C   Q   E   T       S   Q   T       G   R   D
 61  TACGCTCAGC AGACTCGAGG TGAGGAGGGT TGCCAAGAAA CCTCCCAGAC CGGTCGTGAC
     ATGCGAGTCG TCTGAGCTCC ACTCCTCCCA ACGGTTCTTT GGAGGGTCTG GCCAGCACTG

K   N   Q       V   E   G   E       V   Q   I       V   S   T   A       T   Q   T       F   L   A
121  AAAAACCAGG TTGAAGGTGA AGTTCAGATC GTTTCCACCG CTACCCAGAC CTTCCTGGCT
     TTTTTGGTCC AACTTCCACT TCAAGTCTAG CAAAGGTGGC GATGGGTCTG GAAGGACCGA

T   S   I   N       G   V   L       W   T   V       Y   H   G   A       G   T   R       T   I   A
181  ACCTCCATCA ACGGTGTTCT GTGGACCGTT TACCACGGTG CTGGTACCCG TACCATCGCT
     TGGAGGTAGT TGCCACAAGA CACCTGGCAA ATGGTGCCAC GACCATGGGC ATGGTAGCGA

S   P   K   G       P   V   T       Q   M   Y       T   N   V   D       K   D   L       V   G   W
241  TCCCCGAAAG GTCCGGTTAC CCAGATGTAC ACCAACGTTG ACAAAGACCT GGTTGGTTGG
     AGGGGCTTTC CAGGCCAATG GGTCTACATG TGGTTGCAAC TGTTTCTGGA CCAACCAACC

Q   A   P   Q       G   S   R       S   L   T       P   C   T   C       G   S   S       D   L   Y
301  CAGGCTCCGC AGGGTTCCCG TTCCCTGACC CCGTGCACCT GCGGTTCCTC CGACCTGTAC
     GTCCGAGGCG TCCCAAGGGC AAGGGACTGG GGCACGTGGA CGCCAAGGAG GCTGGACATG

L   V   T       R   H   A   D       V   I   P       V   R   R   R       G   D   S       R   G   S
361  CTGGTTACCC GTCACGCTGA CGTTATCCCG GTTCGTCGTC GTGGTGACTC CCGTGGTTCC
     GACCAATGGG CAGTGCGACT GCAATAGGGC CAAGCAGCAG CACCACTGAG GGCACCAAGG

L   L   S   P       R   P   I       S   Y   L       K   G   S   S       G   G   P       L   L   C
421  CTGCTGTCCC CGCGTCCGAT CTCCTACCTG AAAGGTTCCT CCGGTGGTCC GCTGCTGTGC
     GACGACAGGG GCGCAGGCTA GAGGATGGAC TTTCCAAGGA GGCCACCAGG CGACGACACG

P   A   G   H       A   V   G       I   F   R       A   A   V   S       T   R   G       V   A   K
481  CCGGCTGGTC ACGCTGTTGG TATCTTCCGT GCTGCTGTTT CCACCCGTGG TGTTGCTAAA
     GGCCGACCAG TGCGACAACC ATAGAAGGCA CGACGACAAA GGTGGGCACC ACAACGATTT

A   V   D   F       I   P   V       E   S   L       E   T   T   M       R   S   P       *
541  GCTGTTGACT TCATCCCGGT TGAATCCCTG GAAACCACCA TGCGTTCCCC GTGA
     CGACAACTGA AGTAGGGCCA ACTTAGGGAC CTTTGGTGGT ACGCAAGGGG CACT
```

FIG. 15

```
      M   K   K   K       G   S   V       V   I   V       G   R   I   N       L   S   G       D   T   A
  1 ATGAAAAAAA AAGGATCCGT TGTTATCGTC GGCCGTATCA ACCTGTCCGG TGACACCGCT
    TACTTTTTTT TTCCTAGGCA ACAATAGCAG CCGGCATAGT TGGACAGGCC ACTGTGGCGA

Y   A   Q   Q       T   R   G       E   Q   G       C   Q   K   T       S   H   T       G   R   D
 61 TACGCTCAGC AGACTCGAGG TGAGCAGGGT TGCCAGAAGA CCTCCCACAC CGGTCGTGAC
    ATGCGAGTCG TCTGAGCTCC ACTCGTCCCA ACGGTCTTCT GGAGGGTGTG GCCAGCACTG

K   N   Q       V   E   G   E       V   Q   I       V   S   T       A   T   Q       T   F   L   A
121 AAAAACCAGG TTGAAGGTGA AGTTCAGATC GTTTCCACCG CTACCCAGAC CTTCCTGGCT
    TTTTTGGTCC AACTTCCACT TCAAGTCTAG CAAAGGTGGC GATGGGTCTG GAAGGACCGA

T   S   I   N       G   V   L       W   T   V       Y   H   G       A   G   T   R       T   I   A
181 ACCTCCATCA ACGGTGTTCT GTGGACCGTT TACCACGGTG CTGGTACCCG TACCATCGCT
    TGGAGGTAGT TGCCACAAGA CACCTGGCAA ATGGTGCCAC GACCATGGGC ATGGTAGCGA

S   P   K   G       P   V   T       Q   M   Y       T   N   V       D   K   D   L       V   G   W
241 TCCCCGAAAG GTCCGGTTAC CCAGATGTAC ACCAACGTTG ACAAAGACCT GGTTGGTTGG
    AGGGGCTTTC CAGGCCAATG GGTCTACATG TGGTTGCAAC TGTTTCTGGA CCAACCAACC

Q   A   P   Q       G   S   R       S   L   T       P   C   T       C   G   S   S       D   L   Y
301 CAGGCTCCGC AGGGTTCCCG TTCCCTGACC CCGTGCACCT GCGGTTCCTC CGACCTGTAC
    GTCCGAGGCG TCCCAAGGGC AAGGGACTGG GGCACGTGGA CGCCAAGGAG GCTGGACATG

L   V   T   R       H   A   D       V   I   P       V   R   R       R   G   D   S       R   G   S
361 CTGGTTACCC GTCACGCTGA CGTTATCCCG GTTCGTCGTC GTGGTGACTC CCGTGGTTCC
    GACCAATGGG CAGTGCGACT GCAATAGGGC CAAGCAGCAG CACCACTGAG GGCACCAAGG

L   L   S   P       R   P   I       S   Y   L       K   G   S   S       G   G   P       L   L   C
421 CTGCTGTCCC CGCGTCCGAT CTCCTACCTG AAAGGTTCCT CCGGTGGTCC GCTGCTGTGC
    GACGACAGGG GCGCAGGCTA GAGGATGGAC TTTCCAAGGA GGCCACCAGG CGACGACACG

P   A   G   H       A   V   G       I   F   R       A   A   V   S       T   R   G       V   A   K
481 CCGGCTGGTC ACGCTGTTGG TATCTTCCGT GCTGCTGTTT CCACCCGTGG TGTTGCTAAA
    GGCCGACCAG TGCGACAACC ATAGAAGGCA CGACGACAAA GGTGGGCACC ACAACGATTT

A   V   D   F       I   P   V       E   S   L       E   T   T       M   R   S   P   *
541 GCTGTTGACT TCATCCCGGT TGAATCCCTG GAAACCACCA TGCGTTCCCC GTGA
    CGACAACTGA AGTAGGGCCA ACTTAGGGAC CTTTGGTGGT ACGCAAGGGG CACT
```

FIG. 16

```
      M  K  K  K     G  S  V     V  I  V     G  R  I  N     L  S  G     D  T  A
  1 ATGAAAAAAA AAGGATCCGT TGTTATCGTC GGCCGTATCA ACCTGTCCGG TGACACCGCT
    TACTTTTTTT TTCCTAGGCA ACAATAGCAG CCGGCATAGT TGGACAGGCC ACTGTGGCGA

Y  A  Q  Q     T  R  G     E  Q  G     T  Q  K  T     S  H  T     G  R  D
 61 TACGCTCAGC AGACTCGAGG TGAGCAGGGT ACCCAGAAGA CCTCCCACAC CGGTCGTGAC
    ATGCGAGTCG TCTGAGCTCC ACTCGTCCCA TGGGTCTTCT GGAGGGTGTG GCCAGCACTG

K  N  Q  V     E  G  E     V  Q  I     V  S  T  A     T  Q  T     F  L  A
121 AAAAACCAGG TTGAAGGTGA AGTTCAGATC GTTTCCACCG CTACCCAGAC CTTCCTGGCT
    TTTTTGGTCC AACTTCCACT TCAAGTCTAG CAAAGGTGGC GATGGGTCTG GAAGGACCGA

T  S  I  N     G  V  L     W  T  V     Y  H  G  A     G  T  R     T  I  A
181 ACCTCCATCA ACGGTGTTCT GTGGACCGTT TACCACGGTG CTGGTACCCG TACCATCGCT
    TGGAGGTAGT TGCCACAAGA CACCTGGCAA ATGGTGCCAC GACCATGGGC ATGGTAGCGA

S  P  K  G     P  V  T     Q  M  Y     T  N  V  D     K  D  L     V  G  W
241 TCCCCGAAAG GTCCGGTTAC CCAGATGTAC ACCAACGTTG ACAAAGACCT GGTTGGTTGG
    AGGGGCTTTC CAGGCCAATG GGTCTACATG TGGTTGCAAC TGTTTCTGGA CCAACCAACC

Q  A  P  Q     G  S  R     S  L  T     P  C  T  C     G  S  S     D  L  Y
301 CAGGCTCCGC AGGGTTCCCG TTCCCTGACC CCGTGCACCT GCGGTTCCTC CGACCTGTAC
    GTCCGAGGCG TCCCAAGGGC AAGGGACTGG GGCACGTGGA CGCCAAGGAG GCTGGACATG

L  V  T  R     H  A  D     V  I  P     V  R  R  R     G  D  S     R  G  S
361 CTGGTTACCC GTCACGCTGA CGTTATCCCG GTTCGTCGTC GTGGTGACTC CCGTGGTTCC
    GACCAATGGG CAGTGCGACT GCAATAGGGC CAAGCAGCAG CACCACTGAG GGCACCAAGG

L  L  S  P     R  P  I     S  Y  L     K  G  S  S     G  G  P     L  L  C
421 CTGCTGTCCC GCGTCCGAT CTCCTACCTG AAAGGTTCCT CCGGTGGTCC GCTGCTGTGC
    GACGACAGGG GCGCAGGCTA GAGGATGGAC TTTCCAAGGA GGCCACCAGG CGACGACACG

P  A  G  H     A  V  G     I  F  R     A  A  V  S     T  R  G     V  A  K
481 CCGGCTGGTC ACGCTGTTGG TATCTTCCGT GCTGCTGTTT CCACCCGTGG TGTTGCTAAA
    GGCCGACCAG TGCGACAACC ATAGAAGGCA CGACGACAAA GGTGGGCACC ACAACGATTT

A  V  D  F     I  P  V     E  S  L     E  T  T  M     R  S  P     *
541 GCTGTTGACT TCATCCCGGT TGAATCCCTG GAAACCACCA TGCGTTCCCC GTGA
    CGACAACTGA AGTAGGGCCA ACTTAGGGAC CTTTGGTGGT ACGCAAGGGG CACT
```

FIG. 17

```
      M   K   K   K   G   S   V       V   I   V       G   R   I   N       L   S   G       D   T   A
  1 ATGAAAAAAA AAGGATCCGT TGTTATCGTC GGCCGTATCA ACCTGTCCGG TGACACCGCT
    TACTTTTTTT TTCCTAGGCA ACAATAGCAG CCGGCATAGT TGGACAGGCC ACTGTGGCGA

Y   A   Q   Q       T   R   G       L   L   G       C   I   I   T       S   L   T       G   R   D
 61 TACGCTCAGC AGACTCGAGG TCTGCTGGGT TGCATCATCA CCTCCCTGAC CGGTCGTGAC
    ATGCGAGTCG TCTGAGCTCC AGACGACCCA ACGTAGTAGT GGAGGGACTG GCCAGCACTG

K   N   Q   V       E   G   E       V   Q   I       V   S   T   A       A   Q   T       F   L   A
121 AAAAACCAGG TTGAAGGTGA AGTTCAGATC GTTTCCACCG CTGCTCAGAC CTTCCTGGCT
    TTTTTGGTCC AACTTCCACT TCAAGTCTAG CAAAGGTGGC GACGAGTCTG GAAGGACCGA

T   C   I   N       G   V   C       W   T   V       Y   H   G   A       G   T   R       T   I   A
181 ACCTGCATCA ACGGTGTTTG CTGGACCGTT TACCACGGTG CTGGTACCCG TACCATCGCT
    TGGACGTAGT TGCCACAAAC GACCTGGCAA ATGGTGCCAC GACCATGGGC ATGGTAGCGA

S   P   K   G       P   V   I       Q   M   Y       T   N   V   D       K   D   L       V   G   W
241 TCCCCGAAAG GTCCGGTTAT CCAGATGTAC ACCAACGTTG ACAAAGACCT GGTTGGTTGG
    AGGGGCTTTC CAGGCCAATA GGTCTACATG TGGTTGCAAC TGTTTCTGGA CCAACCAACC

P   A   P   Q       G   S   R       S   L   T       P   C   T   G       S   S   D       L   Y
301 CCGGCTCCGC AGGGTTCCCG TTCCCTGACC CCGTGCACCT GCGGTTCCTC CGACCTGTAC
    GGCCGAGGCG TCCCAAGGGC AAGGGACTGG GGCACGTGGA CGCCAAGGAG GCTGGACATG

L   V   T   R       H   A   D       V   I   P       V   R   R   R       G   D   S       R   G   S
361 CTGGTTACCC GTCACGCTGA CGTTATCCCG GTTCGTCGTC GTGGTGACTC CCGTGGTTCC
    GACCAATGGG CAGTGCGACT GCAATAGGGC CAAGCAGCAG CACCACTGAG GGCACCAAGG

L   L   S   P       R   P   I       S   Y   L       K   G   S   S       G   P   L       L   C
421 CTGCTGTCCC CGCGTCCGAT CTCCTACCTG AAAGGTTCCT CCGGTGGTCC GCTGCTGTGC
    GACGACAGGG GCGCAGGCTA GAGGATGGAC TTTCCAAGGA GGCCACCAGG CGACGACACG

P   A   G   H       A   V   G       I   F   R       A   A   V   C       T   R   G       V   A   K
481 CCGGCTGGTC ACGCTGTTGG TATCTTCCGT GCTGCTGTTT GCACCCGTGG TGTTGCTAAA
    GGCCGACCAG TGCGACAACC ATAGAAGGCA CGACGACAAA CGTGGGCACC ACAACGATTT

A   V   D   F       I   P   V       E   S   L       E   T   T   M       R   S   P       *
541 GCTGTTGACT TCATCCCGGT TGAATCCCTG GAAACCACCA TGCGTTCCCC GTGA
    CGACAACTGA AGTAGGGCCA ACTTAGGGAC CTTTGGTGGT ACGCAAGGGG CACT
```

FIG. 18

SEQUENCE LISTING

<160> NUMBER OF SEQ ID NOS: 26

<210> SEQ ID NO 1
<211> LENGTH: 182
<212> TYPE: PRT
<213> ORGANISM: Hepatitis C virus

<400> SEQUENCE: 1

```
Met Ala Pro Ile Thr Ala Tyr Ala Gln Gln Thr Arg Gly Leu Leu Gly
 1               5                  10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60
```

```
Ile Ala Ser Pro Lys Gly Pro Val Ile Gln Met Tyr Thr Asn Val Asp
 65                  70                  75                  80

Lys Asp Leu Val Gly Trp Pro Ala Pro Gln Gly Ser Arg Ser Leu Thr
                 85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Ile Ser Tyr Leu Lys Gly Ser Ser Gly Pro Leu
130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Ser Leu
                165                 170                 175

Glu Thr Thr Met Arg Ser
            180

<210> SEQ ID NO 2
<211> LENGTH: 549
<212> TYPE: DNA
<213> ORGANISM: Hepatitis C virus

<400> SEQUENCE: 2
atggctccga tcaccgctta cgctcagcag acccgtggtc tgctgggttg catcatcacc       60
tccctgaccg gtcgtgacaa aaccaggtt gaaggtgaag ttcagatcgt ttccaccgct      120
gctcagacct tcctggctac ctgcatcaac ggtgtttgct ggaccgttta ccacggtgct      180
ggtacccgta ccatcgcttc cccgaaaggt ccggttatcc agatgtacac caacgttgac      240
aaagacctgg ttggttggcc ggctccgcag ggttcccgtt ccctgacccc gtgcacctgc      300
ggttcctccg acctgtacct ggttacccgt cacgctgacg ttatcccggt tcgtcgtcgt      360
ggtgactccc gtggttccct gctgtccccg cgtccgatct cctacctgaa aggttcctcc      420
ggtggtccgc tgctgtgccc ggctggtcac gctgttggta tcttccgtgc tgctgtttgc      480
acccgtggtg ttgctaaagc tgttgacttc atcccggttg aatccctgga aaccaccatg      540
cgttcctga                                                              549

<210> SEQ ID NO 3
<211> LENGTH: 195
<212> TYPE: PRT
<213> ORGANISM: Hepatitis C virus

<400> SEQUENCE: 3

Met Lys Lys Lys Gly Ser Val Val Ile Val Gly Arg Ile Val Leu Asn
  1               5                  10                  15

Gly Ala Tyr Ala Gln Gln Thr Arg Gly Leu Leu Gly Cys Ile Ile Thr
             20                  25                  30

Ser Leu Thr Gly Arg Asp Lys Asn Gln Val Glu Gly Glu Val Gln Ile
         35                  40                  45

Val Ser Thr Ala Ala Gln Thr Phe Leu Ala Thr Cys Ile Asn Gly Val
     50                  55                  60

Cys Trp Thr Val Tyr His Gly Ala Gly Thr Arg Thr Ile Ala Ser Pro
 65                  70                  75                  80

Lys Gly Pro Val Ile Gln Met Tyr Thr Asn Val Asp Lys Asp Leu Val
                 85                  90                  95

Gly Trp Pro Ala Pro Gln Gly Ser Arg Ser Leu Thr Pro Cys Thr Cys
```

```
                100             105             110
Gly Ser Ser Asp Leu Tyr Leu Val Thr Arg His Ala Asp Val Ile Pro
            115                 120             125

Val Arg Arg Gly Asp Ser Arg Gly Ser Leu Leu Ser Pro Arg Pro
    130                 135                 140

Ile Ser Tyr Leu Lys Gly Ser Ser Gly Gly Pro Leu Leu Cys Pro Ala
145                 150                 155                 160

Gly His Ala Val Gly Ile Phe Arg Ala Ala Val Cys Thr Arg Gly Val
                165                 170                 175

Ala Lys Ala Val Asp Phe Ile Pro Val Glu Ser Leu Glu Thr Thr Met
                180                 185                 190

Arg Ser Pro
        195

<210> SEQ ID NO 4
<211> LENGTH: 588
<212> TYPE: DNA
<213> ORGANISM: Hepatitis C virus

<400> SEQUENCE: 4
atgaaaaaaa aaggttccgt tgttatcgtc ggccgtatag tactgaacgg tgcttacgct      60
cagcagactc gaggtctgct gggttgcatc atcacctccc tgaccggtcg tgacaaaaac     120
caggttgaag gtgaagttca gatcgttttc accgctgctc agaccttcct ggctacctgc     180
atcaacggtg tttgctggac cgtttaccac ggtgctggta cccgtaccat cgcttccccg     240
aaaggtccgg ttatccagat gtacaccaac gttgacaaag acctggttgg ttggccggct     300
ccgcagggtt cccgttccct gaccccgtgc acctgcggtt cctccgacct gtacctggtt     360
acccgtcacg ctgacgttat cccggttcgt cgtcgtggtg actcccgtgg ttccctgctg     420
tccccgcgtc cgatctccta cctgaaaggt tcctccggtg gtccgctgct gtgcccggct     480
ggtcacgctg ttggtatctt ccgtgctgct gtttgcaccc gtggtgttgc taaagctgtt     540
gacttcatcc cggttgaatc cctggaaacc accatgcgtt ccccgtga               588

<210> SEQ ID NO 5
<211> LENGTH: 15
<212> TYPE: PRT
<213> ORGANISM: Hepatitis C virus

<400> SEQUENCE: 5

Gln Gln Thr Arg Gly Leu Leu Gly Cys Ile Ile Thr Ser Leu Thr
1               5                   10                  15

<210> SEQ ID NO 6
<211> LENGTH: 15
<212> TYPE: PRT
<213> ORGANISM: Hepatitis C virus

<400> SEQUENCE: 6

Gln Gln Thr Arg Gly Glu Glu Gly Cys Gln Glu Thr Ser Gln Thr
1               5                   10                  15

<210> SEQ ID NO 7
<211> LENGTH: 15
<212> TYPE: PRT
<213> ORGANISM: Hepatitis C virus

<400> SEQUENCE: 7

Gln Gln Thr Arg Gly Glu Glu Gly Cys Gln Gln Thr Ser Glu Thr
```

```
<210> SEQ ID NO 8
<211> LENGTH: 15
<212> TYPE: PRT
<213> ORGANISM: Hepatitis C virus

<400> SEQUENCE: 8

Gln Gln Thr Arg Gly Asn Gln Gly Cys Glu Lys Thr Ser Glu Thr
 1               5                  10                  15

<210> SEQ ID NO 9
<211> LENGTH: 15
<212> TYPE: PRT
<213> ORGANISM: Hepatitis C virus

<400> SEQUENCE: 9

Gln Gln Thr Arg Gly Glu Gln Gly Cys Gln Lys Thr Ser His Thr
 1               5                  10                  15

<210> SEQ ID NO 10
<211> LENGTH: 15
<212> TYPE: PRT
<213> ORGANISM: Hepatitis C virus

<400> SEQUENCE: 10

Gln Gln Thr Arg Gly Glu Gln Gly Cys Asp Glu Thr Ser Glu Thr
 1               5                  10                  15

<210> SEQ ID NO 11
<211> LENGTH: 15
<212> TYPE: PRT
<213> ORGANISM: Hepatitis C virus

<400> SEQUENCE: 11

Gln Gln Thr Arg Gly Glu Glu Gly Cys Glu Gln Thr Ser Glu Thr
 1               5                  10                  15

<210> SEQ ID NO 12
<211> LENGTH: 195
<212> TYPE: PRT
<213> ORGANISM: Hepatitis C virus

<400> SEQUENCE: 12

Met Lys Lys Lys Gly Ser Val Val Ile Val Gly Arg Ile Val Leu Asn
 1               5                  10                  15

Gly Ala Tyr Ala Gln Gln Thr Arg Gly Glu Glu Gly Cys Gln Glu Thr
                20                  25                  30

Ser Gln Thr Gly Arg Asp Lys Asn Gln Val Glu Gly Glu Val Gln Ile
                35                  40                  45

Val Ser Thr Ala Ala Gln Thr Phe Leu Ala Thr Cys Ile Asn Gly Val
        50                  55                  60

Cys Trp Thr Val Tyr His Gly Ala Gly Thr Arg Thr Ile Ala Ser Pro
65                  70                  75                  80

Lys Gly Pro Val Ile Gln Met Tyr Thr Asn Val Asp Lys Asp Leu Val
                85                  90                  95

Gly Trp Pro Ala Pro Gln Gly Ser Arg Ser Leu Thr Pro Cys Thr Cys
                100                 105                 110

Gly Ser Ser Asp Leu Tyr Leu Val Thr Arg His Ala Asp Val Ile Pro
                115                 120                 125

Val Arg Arg Arg Gly Asp Ser Arg Gly Ser Leu Leu Ser Pro Arg Pro
```

```
                130                 135                 140
Ile Ser Tyr Leu Lys Gly Ser Ser Gly Gly Pro Leu Leu Cys Pro Ala
145                 150                 155                 160

Gly His Ala Val Gly Ile Phe Arg Ala Ala Val Cys Thr Arg Gly Val
                165                 170                 175

Ala Lys Ala Val Asp Phe Ile Pro Val Glu Ser Leu Glu Thr Thr Met
                180                 185                 190

Arg Ser Pro
        195

<210> SEQ ID NO 13
<211> LENGTH: 588
<212> TYPE: DNA
<213> ORGANISM: Hepatitis C virus

<400> SEQUENCE: 13
atgaaaaaaa aaggatccgt tgttatcgtc ggccgtatag tactgaacgg tgcttacgct      60
cagcagactc gaggtgagga gggttgccaa gaaacctccc agaccggtcg tgacaaaaac     120
caggttgaag gtgaagttca gatcgtttcc accgctgctc agaccttcct ggctacctgc     180
atcaacggtg tttgctggac cgtttaccac ggtgctggta cccgtaccat cgcttccccg     240
aaaggtccgg ttatccagat gtacaccaac gttgacaaag acctggttgg ttggccggct     300
ccgcagggtt cccgttccct gaccccgtgc acctgcggtt cctccgacct gtacctggtt     360
acccgtcacg ctgacgttat cccggttcgt cgtcgtggtg actcccgtgg ttccctgctg     420
tccccgcgtc cgatctccta cctgaaaggt tcctccggtg gtccgctgct gtgcccggct     480
ggtcacgctg ttggtatctt ccgtgctgct gtttgcaccc gtggtgttgc taaagctgtt     540
gacttcatcc cggttgaatc cctggaaacc accatgcgtt ccccgtga               588

<210> SEQ ID NO 14
<211> LENGTH: 197
<212> TYPE: PRT
<213> ORGANISM: Hepatitis C virus

<400> SEQUENCE: 14

Met Lys Lys Lys Gly Ser Val Val Ile Val Gly Arg Ile Asn Leu Ser
  1               5                  10                  15

Gly Asp Thr Ala Tyr Ala Gln Gln Thr Arg Gly Glu Glu Gly Cys Gln
                 20                  25                  30

Glu Thr Ser Gln Thr Gly Arg Asp Lys Asn Gln Val Glu Gly Glu Val
             35                  40                  45

Gln Ile Val Ser Thr Ala Ala Gln Thr Phe Leu Ala Thr Cys Ile Asn
         50                  55                  60

Gly Val Cys Trp Thr Val Tyr His Gly Ala Gly Thr Arg Thr Ile Ala
 65                  70                  75                  80

Ser Pro Lys Gly Pro Val Ile Gln Met Tyr Thr Asn Val Asp Lys Asp
                 85                  90                  95

Leu Val Gly Trp Pro Ala Pro Gln Gly Ser Arg Ser Leu Thr Pro Cys
                100                 105                 110

Thr Cys Gly Ser Ser Asp Leu Tyr Leu Val Thr Arg His Ala Asp Val
            115                 120                 125

Ile Pro Val Arg Arg Arg Gly Asp Ser Arg Gly Ser Leu Leu Ser Pro
        130                 135                 140

Arg Pro Ile Ser Tyr Leu Lys Gly Ser Ser Gly Gly Pro Leu Leu Cys
145                 150                 155                 160
```

```
Pro Ala Gly His Ala Val Gly Ile Phe Arg Ala Ala Val Cys Thr Arg
            165                 170                 175

Gly Val Ala Lys Ala Val Asp Phe Ile Pro Val Glu Ser Leu Glu Thr
        180                 185                 190

Thr Met Arg Ser Pro
        195

<210> SEQ ID NO 15
<211> LENGTH: 594
<212> TYPE: DNA
<213> ORGANISM: Hepatitis C virus

<400> SEQUENCE: 15
atgaaaaaaa aaggatccgt tgttatcgtc ggccgtatca acctgtccgg tgacaccgct      60
tacgctcagc agactcgagg tgaggagggt tgccaagaaa cctcccagac cggtcgtgac     120
aaaaaccagg ttgaaggtga agttcagatc gtttccaccg ctgctcagac cttcctggct     180
acctgcatca acggtgtttg ctggaccgtt taccacggtg ctggtacccg taccatcgct     240
tccccgaaag gtccggttat ccagatgtac accaacgttg acaaagacct ggttggttgg     300
ccggctccgc agggttcccg ttccctgacc ccgtgcacct gcggttcctc cgacctgtac     360
ctggttaccc gtcacgctga cgttatcccg gttcgtcgtc gtggtgactc ccgtggttcc     420
ctgctgtccc cgcgtccgat ctcctacctg aaaggttcct ccggtggtcc gctgctgtgc     480
ccggctggtc acgctgttgg tatcttccgt gctgctgttt gcacccgtgg tgttgctaaa     540
gctgttgact catcccggt tgaatccctg gaaaccacca tgcgttcccc gtga            594

<210> SEQ ID NO 16
<211> LENGTH: 197
<212> TYPE: PRT
<213> ORGANISM: Hepatitis C virus

<400> SEQUENCE: 16

Met Lys Lys Lys Gly Ser Val Val Ile Val Gly Arg Ile Asn Leu Ser
  1               5                  10                  15

Gly Asp Thr Ala Tyr Ala Gln Gln Thr Arg Gly Glu Glu Gly Cys Gln
            20                  25                  30

Glu Thr Ser Gln Thr Gly Arg Asp Lys Asn Gln Val Glu Gly Glu Val
        35                  40                  45

Gln Ile Val Ser Thr Ala Thr Gln Thr Phe Leu Ala Thr Cys Ile Asn
    50                  55                  60

Gly Val Cys Trp Thr Val Tyr His Gly Ala Gly Thr Arg Thr Ile Ala
 65                  70                  75                  80

Ser Pro Lys Gly Pro Val Thr Gln Met Tyr Thr Asn Val Asp Lys Asp
                85                  90                  95

Leu Val Gly Trp Gln Ala Pro Gln Gly Ser Arg Ser Leu Thr Pro Cys
            100                 105                 110

Thr Cys Gly Ser Ser Asp Leu Tyr Leu Val Thr Arg His Ala Asp Val
        115                 120                 125

Ile Pro Val Arg Arg Arg Gly Asp Ser Arg Gly Ser Leu Leu Ser Pro
    130                 135                 140

Arg Pro Ile Ser Tyr Leu Lys Gly Ser Ser Gly Gly Pro Leu Leu Cys
145                 150                 155                 160

Pro Ala Gly His Ala Val Gly Ile Phe Arg Ala Ala Val Cys Thr Arg
            165                 170                 175
```

Gly Val Ala Lys Ala Val Asp Phe Ile Pro Val Glu Ser Leu Glu Thr
            180                 185                 190

Thr Met Arg Ser Pro
        195

<210> SEQ ID NO 17
<211> LENGTH: 594
<212> TYPE: DNA
<213> ORGANISM: Hepatitis C virus

<400> SEQUENCE: 17

| | | |
|---|---|---|
| atgaaaaaaa aaggatccgt tgttatcgtc ggccgtatca acctgtccgg tgacaccgct | 60 |
| tacgctcagc agactcgagg tgaggagggt tgccaagaaa cctcccagac cggtcgtgac | 120 |
| aaaaaccagg ttgaaggtga agttcagatc gtttccaccg ctacccagac cttcctggct | 180 |
| acctgcatca acggtgtttg ctggaccgtt taccacggtg ctggtacccg taccatcgct | 240 |
| tccccgaaag gtccggttac ccagatgtac accaacgttg acaaagacct ggttggttgg | 300 |
| caggctccgc agggtccccg ttccctgacc ccgtgcacct gcggttcctc cgacctgtac | 360 |
| ctggttaccc gtcacgctga cgttatcccg gttcgtcgtc gtggtgactc ccgtggttcc | 420 |
| ctgctgtccc cgcgtccgat ctcctacctg aaaggttcct ccggtggtcc gctgctgtgc | 480 |
| ccggctggtc acgctgttgg tatcttccgt gctgctgttt gcacccgtgg tgttgctaaa | 540 |
| gctgttgact tcatcccggt tgaatccctg gaaaccacca tgcgttcccc gtga | 594 |

<210> SEQ ID NO 18
<211> LENGTH: 197
<212> TYPE: PRT
<213> ORGANISM: Hepatitis C virus

<400> SEQUENCE: 18

Met Lys Lys Lys Gly Ser Val Val Ile Val Gly Arg Ile Asn Leu Ser
 1               5                  10                  15

Gly Asp Thr Ala Tyr Ala Gln Gln Thr Arg Gly Glu Glu Gly Cys Gln
            20                  25                  30

Glu Thr Ser Gln Thr Gly Arg Asp Lys Asn Gln Val Glu Gly Glu Val
        35                  40                  45

Gln Ile Val Ser Thr Ala Thr Gln Thr Phe Leu Ala Thr Ser Ile Asn
    50                  55                  60

Gly Val Leu Trp Thr Val Tyr His Gly Ala Gly Thr Arg Thr Ile Ala
65                  70                  75                  80

Ser Pro Lys Gly Pro Val Thr Gln Met Tyr Thr Asn Val Asp Lys Asp
                85                  90                  95

Leu Val Gly Trp Gln Ala Pro Gln Gly Ser Arg Ser Leu Thr Pro Cys
            100                 105                 110

Thr Cys Gly Ser Ser Asp Leu Tyr Leu Val Thr Arg His Ala Asp Val
        115                 120                 125

Ile Pro Val Arg Arg Arg Gly Asp Ser Arg Gly Ser Leu Leu Ser Pro
    130                 135                 140

Arg Pro Ile Ser Tyr Leu Lys Gly Ser Ser Gly Gly Pro Leu Leu Cys
145                 150                 155                 160

Pro Ala Gly His Ala Val Gly Ile Phe Arg Ala Ala Val Cys Thr Arg
                165                 170                 175

Gly Val Ala Lys Ala Val Asp Phe Ile Pro Val Glu Ser Leu Glu Thr
            180                 185                 190

Thr Met Arg Ser Pro
        195

-continued

```
            195
```

```
<210> SEQ ID NO 19
<211> LENGTH: 594
<212> TYPE: DNA
<213> ORGANISM: Hepatitis C virus

<400> SEQUENCE: 19
atgaaaaaaa aaggatccgt tgttatcgtc ggccgtatca acctgtccgg tgacaccgct     60
tacgctcagc agactcgagg tgaggagggt tgccaagaaa cctcccagac cggtcgtgac    120
aaaaaccagg ttgaaggtga agttcagatc gtttccaccg ctacccagac cttcctggct    180
acctccatca acggtgttct gtggaccgtt taccacggtg ctggtacccg taccatcgct    240
tccccgaaag gtccggttac ccagatgtac accaacgttg acaaagacct ggttggttgg    300
caggctccgc agggttcccg ttccctgacc ccgtgcacct gcggttcctc cgacctgtac    360
ctggttaccc gtcacgctga cgttatcccg gttcgtcgtc gtggtgactc ccgtggttcc    420
ctgctgtccc cgcgtccgat ctcctacctg aaaggttcct ccggtggtcc gctgctgtgc    480
ccggctggtc acgctgttgg tatcttccgt gctgctgttt ccaccgtgg tgttgctaaa     540 gctgttgact tcatcccggt tgaatccctg gaaaccacca tgcgttcccc gtga          594
```

```
<210> SEQ ID NO 20
<211> LENGTH: 197
<212> TYPE: PRT
<213> ORGANISM: Hepatitis C virus

<400> SEQUENCE: 20

Met Lys Lys Lys Gly Ser Val Val Ile Val Gly Arg Ile Asn Leu Ser
  1               5                  10                  15

Gly Asp Thr Ala Tyr Ala Gln Gln Thr Arg Gly Glu Gln Gly Cys Gln
             20                  25                  30

Lys Thr Ser His Thr Gly Arg Asp Lys Asn Gln Val Glu Gly Glu Val
         35                  40                  45

Gln Ile Val Ser Thr Ala Thr Gln Thr Phe Leu Ala Thr Ser Ile Asn
     50                  55                  60

Gly Val Leu Trp Thr Val Tyr His Gly Ala Gly Thr Arg Thr Ile Ala
 65                  70                  75                  80

Ser Pro Lys Gly Pro Val Thr Gln Met Tyr Thr Asn Val Asp Lys Asp
                 85                  90                  95

Leu Val Gly Trp Gln Ala Pro Gln Gly Ser Arg Ser Leu Thr Pro Cys
            100                 105                 110

Thr Cys Gly Ser Ser Asp Leu Tyr Leu Val Thr Arg His Ala Asp Val
        115                 120                 125

Ile Pro Val Arg Arg Arg Gly Asp Ser Arg Gly Ser Leu Leu Ser Pro
    130                 135                 140

Arg Pro Ile Ser Tyr Leu Lys Gly Ser Ser Gly Gly Pro Leu Leu Cys
145                 150                 155                 160

Pro Ala Gly His Ala Val Gly Ile Phe Arg Ala Ala Val Ser Thr Arg
                165                 170                 175

Gly Val Ala Lys Ala Val Asp Phe Ile Pro Val Glu Ser Leu Glu Thr
            180                 185                 190

Thr Met Arg Ser Pro
        195
```

```
<210> SEQ ID NO 21
```

<211> LENGTH: 594
<212> TYPE: DNA
<213> ORGANISM: Hepatitis C virus

<400> SEQUENCE: 21

```
atgaaaaaaa aaggatccgt tgttatcgtc ggccgtatca acctgtccgg tgacaccgct      60
tacgctcagc agactcgagg tgagcagggt tgccagaaga cctcccacac cggtcgtgac     120
aaaaaccagg ttgaaggtga agttcagatc gtttccaccg ctacccagac cttcctggct     180
acctccatca acggtgttct gtggaccgtt taccacggtg ctggtacccg taccatcgct     240
tccccgaaag gtccggttac ccagatgtac accaacgttg acaaagacct ggttggttgg     300
caggctccgc agggttcccg ttccctgacc ccgtgcacct gcggttcctc cgacctgtac     360
ctggttaccc gtcacgctga cgttatcccg gttcgtcgtc gtggtgactc ccgtggttcc     420
ctgctgtccc cgcgtccgat ctcctacctg aaaggttcct ccggtggtcc gctgctgtgc     480
ccggctggtc acgctgttgg tatcttccgt gctgctgttt ccacccgtgg tgttgctaaa     540
gctgttgact tcatcccggt tgaatccctg gaaaccacca tgcgttcccc gtga           594
```

<210> SEQ ID NO 22
<211> LENGTH: 197
<212> TYPE: PRT
<213> ORGANISM: Hepatitis C virus

<400> SEQUENCE: 22

```
Met Lys Lys Lys Gly Ser Val Val Ile Val Gly Arg Ile Asn Leu Ser
 1               5                  10                  15

Gly Asp Thr Ala Tyr Ala Gln Gln Thr Arg Gly Glu Gln Gly Thr Gln
            20                  25                  30

Lys Thr Ser His Thr Gly Arg Asp Lys Asn Gln Val Glu Gly Glu Val
        35                  40                  45

Gln Ile Val Ser Thr Ala Thr Gln Thr Phe Leu Ala Thr Ser Ile Asn
    50                  55                  60

Gly Val Leu Trp Thr Val Tyr His Gly Ala Gly Thr Arg Thr Ile Ala
65                  70                  75                  80

Ser Pro Lys Gly Pro Val Thr Gln Met Tyr Thr Asn Val Asp Lys Asp
                85                  90                  95

Leu Val Gly Trp Gln Ala Pro Gln Gly Ser Arg Ser Leu Thr Pro Cys
            100                 105                 110

Thr Cys Gly Ser Ser Asp Leu Tyr Leu Val Thr Arg His Ala Asp Val
        115                 120                 125

Ile Pro Val Arg Arg Arg Gly Asp Ser Arg Gly Ser Leu Leu Ser Pro
    130                 135                 140

Arg Pro Ile Ser Tyr Leu Lys Gly Ser Ser Gly Gly Pro Leu Leu Cys
145                 150                 155                 160

Pro Ala Gly His Ala Val Gly Ile Phe Arg Ala Ala Val Ser Thr Arg
                165                 170                 175

Gly Val Ala Lys Ala Val Asp Phe Ile Pro Val Glu Ser Leu Glu Thr
            180                 185                 190

Thr Met Arg Ser Pro
        195
```

<210> SEQ ID NO 23
<211> LENGTH: 594
<212> TYPE: DNA
<213> ORGANISM: Hepatitis C virus

<400> SEQUENCE: 23

```
atgaaaaaaa aaggatccgt tgttatcgtc ggccgtatca acctgtccgg tgacaccgct      60
tacgctcagc agactcgagg tgagcagggt acccagaaga cctcccacac cggtcgtgac     120
aaaaaccagg ttgaaggtga agttcagatc gtttccaccg ctacccagac cttcctggct     180
acctccatca acgtgttct gtggaccgtt taccacggtg ctggtacccg taccatcgct     240
tccccgaaag gtccggttac ccagatgtac accaacgttg acaaagacct ggttggttgg     300
caggctccgc agggttcccg ttccctgacc ccgtgcacct gcggttcctc cgacctgtac     360
ctggttaccc gtcacgctga cgttatcccg gttcgtcgtc gtggtgactc ccgtggttcc     420
ctgctgtccc cgcgtccgat ctcctacctg aaaggttcct ccggtggtcc gctgctgtgc     480
ccggctggtc acgctgttgg tatcttccgt gctgctgttt ccacccgtgg tgttgctaaa     540
gctgttgact catcccggt tgaatccctg gaaaccacca tgcgttcccc gtga            594
```

<210> SEQ ID NO 24
<211> LENGTH: 197
<212> TYPE: PRT
<213> ORGANISM: Hepatitis C virus

<400> SEQUENCE: 24

```
Met Lys Lys Lys Gly Ser Val Val Ile Val Gly Arg Ile Asn Leu Ser
  1               5                  10                  15
Gly Asp Thr Ala Tyr Ala Gln Gln Thr Arg Gly Leu Leu Gly Cys Ile
             20                  25                  30
Ile Thr Ser Leu Thr Gly Arg Asp Lys Asn Gln Val Glu Gly Glu Val
         35                  40                  45
Gln Ile Val Ser Thr Ala Ala Gln Thr Phe Leu Ala Thr Cys Ile Asn
     50                  55                  60
Gly Val Cys Trp Thr Val Tyr His Gly Ala Gly Thr Arg Thr Ile Ala
 65                  70                  75                  80
Ser Pro Lys Gly Pro Val Ile Gln Met Tyr Thr Asn Val Asp Lys Asp
                 85                  90                  95
Leu Val Gly Trp Pro Ala Pro Gln Gly Ser Arg Ser Leu Thr Pro Cys
            100                 105                 110
Thr Cys Gly Ser Ser Asp Leu Tyr Leu Val Thr Arg His Ala Asp Val
        115                 120                 125
Ile Pro Val Arg Arg Arg Gly Asp Ser Arg Gly Ser Leu Leu Ser Pro
    130                 135                 140
Arg Pro Ile Ser Tyr Leu Lys Gly Ser Ser Gly Gly Pro Leu Leu Cys
145                 150                 155                 160
Pro Ala Gly His Ala Val Gly Ile Phe Arg Ala Ala Val Cys Thr Arg
                165                 170                 175
Gly Val Ala Lys Ala Val Asp Phe Ile Pro Val Glu Ser Leu Glu Thr
            180                 185                 190
Thr Met Arg Ser Pro
        195
```

<210> SEQ ID NO 25
<211> LENGTH: 594
<212> TYPE: DNA
<213> ORGANISM: Hepatitis C virus

<400> SEQUENCE: 25

```
atgaaaaaaa aaggatccgt tgttatcgtc ggccgtatca acctgtccgg tgacaccgct      60
```

-continued

```
tacgctcagc agactcgagg tctgctgggt tgcatcatca cctccctgac cggtcgtgac    120
aaaaaccagg ttgaaggtga agttcagatc gtttccaccg ctgctcagac cttcctggct    180
acctgcatca acggtgtttg ctggaccgtt taccacggtg ctggtacccg taccatcgct    240
tccccgaaag gtccggttat ccagatgtac accaacgttg acaaagacct ggttggttgg    300
ccggctccgc agggttcccg ttccctgacc ccgtgcacct gcggttcctc cgacctgtac    360
ctggttaccc gtcacgctga cgttatcccg gttcgtcgtc gtggtgactc ccgtggttcc    420
ctgctgtccc cgcgtccgat ctcctacctg aaaggttcct ccggtggtcc gctgctgtgc    480
ccggctggtc acgctgttgg tatcttccgt gctgctgttt gcaccgtgg tgttgctaaa     540 gctgttgact tcatcccggt tgaatccctg gaaaccacca tgcgttcccc gtga           594
```

<210> SEQ ID NO 26
<211> LENGTH: 11
<212> TYPE: PRT
<213> ORGANISM: Hepatitis C virus

<400> SEQUENCE: 26

```
Gly Ser Val Val Ile Val Gly Arg Ile Val Leu
 1               5                   10
```

MODIFIED FORMS OF HEPATITIS C NS3 PROTEASE FOR FACILITATING INHIBITOR SCREENING AND STRUCTURAL STUDIES OF PROTEASE: INHIBITOR COMPLEXES

This application claims priority from provisional U.S. application Ser. No. 60/115,271, filed Jan, 8, 1999, which is incorporated herein by reference in its entirety.

TECHNICAL FIELD OF THE INVENTION

The present invention relates to modified forms of the Hepatitis C NS3 protease. The wild type protease is essential in vivo for viral replication of Hepatitis C. The novel proteins of this invention are useful for screening for inhibitors of the protease and for structural studies of the protease and protease:inhibitor complexes.

BACKGROUND OF THE INVENTION

Hepatitis C virus (HCV) infection is the suspected cause of 90% of all cases of non-A, non-B hepatitis (Choo et al., 1989, Kuo et al., 1989). HCV infection is more common than HIV infection with an incidence rate of 2–15% worldwide. Over 4 million people are infected with HCV in the United States alone. While primary infection with HCV is often asymptomatic, almost all HCV infections progress to a chronic state that persists for decades. A staggering 20–50% are thought to eventually develop chronic liver disease (e.g. cirrhosis) and 20–30% of these cases will lead to liver failure or liver cancer. Up to 12,000 people in the U.S. will die this year from sequelae associated with HCV infection. As the current population ages over the next two decades, the morbidity and mortality associated with HCV are expected to triple. The development of safe and effective treatment(s) for HCV infection is a major unmet medical need.

The established principle for antiviral intervention is the direct inhibition of essential, virally encoded enzymes. The only approved treatment for HCV infection is interferon, however, which indirectly effects HCV infection by altering the host immune response. Interferon treatment is largely ineffective, as a sustained antiviral response is produced in less than 30% of treated patients. A safe and effective antiviral treatment that blocks viral replication directly would likely have a much more beneficial impact on the public health for HCV infection than does interferon treatment. There have been no such inhibitors of HCV replication disclosed, to date. Vaccination to prevent HCV disease has not shown promise due to the lack of efficacy of vaccine candidates for HCV.

Hepatitis C virus is a positive-strand RNA virus of the family Flaviviridae. The HCV genome encodes a single polyprotein of 3033 amino acids, of which residues 1027 to 1657 (631 amino acids) represent the NS3 protein (Choo et al., 1991). The HCV NS3 protein is a site-specific protease that cleaves the HCV polyprotein selectively at four sites related by their primary amino acid sequences (Grakoui et al., 1993a). These cleavages give rise to the mature non-structural (replicative) proteins of HCV, including NS3, NS4A, NS4B, NS5A, and NS5B (Bartenschlager et al., 1993; Grakoui et al., 1993b; Hijikata, et al., 1993a,b; Tomei et al., 1993; Bartenschlager et al., 1994; Eckart et al., 1994; Lin et al., 1994; Manabe, et al 1994). Genetic studies have demonstrated that the homologous NS3 proteases of related viruses (e.g Yellow Fever Virus and Bovine viral diarrhea virus) are absolutely essential for viral replication (Chambers et al., 1990; Xu et al., 1997). Thus, inhibitors of NS3 protease should inhibit HCV replication and would be useful for the discovery and development of effective antiviral treatments for HCV infection.

Efficient processing of the HCV polyprotein by NS3 also requires the NS4A protein, amino acids 1658–1712 (58 amino acids) of the HCV polyprotein (Bartenschlager et al., 1994; Overton et al., 1994; Bartenschlager et al., 1995; Bouffard et al., 1995; Tanji et al., 1995). NS4A stimulates protease activity through the formation of a heteromeric complex with NS3 (Bartenschlager et al., 1995; Lin et al 1995; Satoh et al., 1995). NS4A is also thought to target the localization of the NS3 protease to the ER membrane, the likely site of viral replication (Hijikata et al., 1993b; Lin and Rice, 1995; Tanji et al., 1995). Studies to map the functional domains of NS3 and NS4A have demonstrated that the protease catalytic domain of NS3 resides within amino acids 1–181 (Bartenschlager et al., 1994; Tanji et al., 1994; Failla et al., 1995; Shoji et al., 1995) and that the catalytic domain interacts with, and is stimulated by, NS4A (Hijikata et al., 1993a; Lin et al., 1994; Bartenschlager et al., 1995; Failla et al., 1995; Satoh et al., 1995; Tanji et al., 1995). The remaining 450 amino acids of NS3 comprise a functional domain with helicase and ATPase activities which are thought to be involved in viral genome replication (Jin and Peterson, 1995). Functional studies of NS4A in vitro demonstrated that the protease stimulatory activity mapped to amino acids 21–34 of NS4A (Lin et al., 1995; Tomei et al., 1995; Shimizu et al., 1996). The N-terminal 20 amino acids of NS4A, on the other hand, are largely hydrophobic in nature and might serve as a transmembrane anchor domain (Lin and Rice, 1995).

The three-dimensional structure of the protease catalytic domain of NS3 has been determined by X-ray crystallography, with and without a cofactor peptide from NS4A (Kim et al., 1996; Love et al., 1996; Yan et al., 1998). These structures revealed very strong structural homology to chymotrypsin-like serine protease domains with the canonical catalytic triad comprising Ser-139, His-57, and Asp-81. The N-terminal 28 amino acids of NS3 were unique, however, as they were unstructured in the absence of NS4A, while in the presence of NS4A peptide this region adopts β-strand and α-helix secondary structures. The co-crystal structure revealed that the NS4A peptide is inserted into, and partially buried by, adjacent β-strands of NS3. Local rearrangements near the protease active site also occur as a result of NS4A binding, and these are thought to render the protease more catalytically active. Thus, NS4A would be expected to stabilize the active conformation of the HCV protease.

Near the N-terminus of NS3 is an (α-helix spanning residues 13–21 ((α-helix 0) that appears to be stabilized by the NS4A peptide. The external face of this helix is very hydrophobic and consists entirely of branched aliphatic residues. Due to its hydrophobic nature, it has been speculated that this surface might be involved in additional membrane interactions for anchoring the NS3:NS4A complex to cytoplasmic membranes (Yan et al., 1998).

Routine methods for the expression of recombinant NS3 protease (e.g E. coli, baculovirus) have been employed widely. A common problem encountered when expressing wild-type NS3 protease (either full-length or truncated catalytic domain) has been the production of either insoluble or poorly soluble protein, especially when using E. coli vector systems. The best systems described to date have produced low levels of recombinant wild-type protease and the protease tends to be poorly soluble (Shoji et al., 1995; Suzuki et al., 1995; Hong et al., 1996; Steinkuhler et al., 1996). As many of these preparations are enzymatically active, this approach has sufficed to generate active enzyme for activity analysis and inhibitor screening. However, to carry out structural studies, highly expressed enzymes characterized by high solubility and low aggregation, in addition to enzymatic activity, are required.

Efforts have been made to overcome problems associated with low expression and/or poor solubility of the HCV protease, by constructing genetically engineered fusion derivatives of the native NS3 protease domain. Most notable are the generation of NS3 protease catalytic domains that form slowly-growing crystals suitable for structure determination by X-ray crystallography (Love et al., 1996; Kim et al., 1996; Yan et al., 1998). These have involved the construction of genetically engineered derivatives of NS3 by fusing polypeptide tags to the N-terminus and/or C-terminus that enhance the stable expression and/or solubility of the expressed protein (e.g. basic amino acids, poly-histidine). Other types of protease fusions (e.g. with ubiquitin, glutathione-S-transferase, maltose binding protein), including fusion of the NS4A protein to the C-terminus of the protease catalytic domain (Inoue etal., 1998), have been described that are partly soluble when expressed in E. coli, but few if any of these have overcome the critical limitation of low overall solubility. Very recently, bacterial expression of constructs in which the NS4a segment is fused to the N-terminus of the NS3 protease have been reported (Taremi et al., 1998; Pasquo et al., 1998); however, overall solubility of the final preparations were not reported.

There has been no published report of a NS3 preparation that is suitable for protein NMR work, as NMR studies typically require protein preparations that are expressed at high levels, are very highly soluble (>1 mM), and do not form soluble aggregates when purified. In addition, no X-ray structures of HCV protease complexed with enzyme inhibitors have been reported to date.

SUMMARY OF THE INVENTION

At this time, no known pharmaceutical agent is available to prevent or cure HCV infection. HCV replication is dependent upon the activity of the virally encoded NS3 protease. Thus, elucidation of a specific inhibitor of this protease activity would be useful for the discovery of drugs to block HCV replication. This can be achieved using one or a combination of methods including, but not limited to: screening for small molecule inhibitors to serve as leads for medicinal chemistry; and the analysis of the three-dimensional structures (by X-ray crystallography or NMR) of complexes between the HCV NS3 protease and compounds that bind to it in efforts to discover insights as to how the compounds might be chemically modified to produce potent inhibitors of this viral protease.

This invention enables the discovery of drugs that prevent or cure HCV infection. This invention encompasses novel, highly soluble, modified forms of HCV NS3 protease. More specifically, this invention includes novel, highly soluble, modified HCV NS3 proteases and novel, highly soluble, modified HCV NS3–NS4a fusion proteases. These novel proteins greatly facilitate screening for small molecule inhibitors and analysis of the three-dimensional structures, through X-ray crystallography and NMR spectroscopy, of complexes between the HCV NS3 protease and compounds that bind to it.

The present invention results from a number of significant modifications made to the wild-type HCV protease sequence.

One aspect of the invention is a modified HCV NS3 protease comprising an HCV NS3 protease comprising at least one substitution in the HICV NS3 protease of a hydrophobic α-helix 0 amino acid residue to a hydrophilic amino acid residue.

Another aspect of the invention is a modified HCV NS4a–NS3 fusion protease comprising a modified HCV NS3 protease fused to a HCV NS4a or modified HCV NS4a.

Further aspects of the invention are nucleic acid molecules encoding the proteins of the present invention, vectors and host cells.

A further aspect of the invention is methods of making proteins of the present invention.

BRIEF DESCRIPTION OF THE FIGURES

FIG. 5. NMR analysis of modified HCV NS4a–NS3 fusion proteases +/– optimized linker. 2D $^1H$-$^{15}N$ HSQC spectra were obtained for $^{15}N$-labeled mutant HCV NS4a–NS3 fusion proteases (all having the Helix0–1 sequence [see FIG. 11—SEQ ID NO:6] and purified as outlined in Example 7). Panel A—with non-optimized linker (see Example 4, SEQ ID NO: 12); Panel B—with optimized linker (see Example 5, SEQ ID NO: 14); Panel C—with optimized linker and A40T, I72T, P86Q, C47S, C52L, C159S mutations (see Example 6, SEQ ID NO:18).

FIG. 6 shows an alignment of the amino acid sequences of SEQ ID Nos: 1, 3, 12, 14, 16, 18, 20, 22 and 24. Bolded letters with stippling indicates residue positions that are mutated relative to SEQ ID NO: 1.

FIG. 8. Portion of the electron density map of a modified HCV NS4a–NS3 fusion protease (SEQ ID NO: 18) complexed with a peptide inhibitor (see Example 10). Two residues of the peptide inhibitor are shown: $Cys_1$ and $Cha_2$.

FIG. 9. Amino acid sequence of (SEQ ID NO: 1) and nucleic acid sequence encoding (SEQ ID NO: 2) the parental non-fusion wild type HCV NS3 protease sequence.

FIG. 10. Amino acid sequence of (SEQ ID NO: 3) and nucleic acid sequence encoding (SEQ ID NO: 4) the initial HCV NS4a–NS3 fusion protease.

FIG. 11. Amino acid sequence (SEQ ID NO: 5) of the α-helix 0 region of wild type HCV NS3 protease, and amino acid sequences of (SEQ ID NOS: 6–11) α-helix 0 regions (helix0-1, helix0-3, helix0-4, helix0-7, helix0-8, and helix0-10 respectively) of various soluble modified HCV NS4a–NS3 fusion proteases that are resistant to high levels of chloramphenicol in the bacterial selection scheme (see Example 4).

FIG. 12. Amino acid sequence of (SEQ ID NO: 12) and nucleic acid sequence encoding (SEQ ID NO: 13) a modified HCV NS4a–NS3 fusion protease with the α-helix 0 variant sequence helix0-1.

FIG. 13. Amino acid sequence of (SEQ ID NO: 14) and nucleic acid sequence encoding (SEQ ID NO: 15) a modified HCV NS4a–NS3 fusion protease with the α-helix 0 variant sequence helix0-1 and an optimized linker sequence.

FIG. 14. Amino acid sequence of (SEQ ID NO: 16) and nucleic acid sequence encoding (SEQ ID NO: 17) a modified HCV NS4a–NS3 fusion protease with the α-helix 0 variant sequence helix0-1, an optimized linker sequence, and surface mutations.

FIG. 15. Amino acid sequence of (SEQ ID NO: 18) and nucleic acid sequence encoding (SEQ ID NO: 19) a modified HCV NS4a–NS3 fusion protease with the α-helix 0 variant sequence helix0-1, an optimized linker sequence, surface mutations, and cysteine mutations.

FIG. 16. Amino acid sequence of (SEQ ID NO: 20) and nucleic acid sequence encoding (SEQ ID NO: 21) a modified HCV NS4a–NS3 fusion protease with the α-helix 0 variant sequence helix0-7, an optimized linker sequence, surface mutations, and cysteine mutations.

FIG. 17. Amino acid sequence of (SEQ ID NO: 22) and nucleic acid sequence encoding (SEQ ID NO: 23) a modified HCV NS4a–NS3 fusion protease with the α-helix 0 variant sequence helix0-7, optimized linker sequence, surface mutations, cysteine mutations and C16T mutation.

FIG. 18. Amino acid sequence of (SEQ ID NO: 24) and nucleic acid sequence encoding (SEQ ID NO: 25) a NS4a–NS3 fusion protein with wild-type (α-helix 0 sequence and optimized linker sequence.

DEFINITIONS

Figure 1:
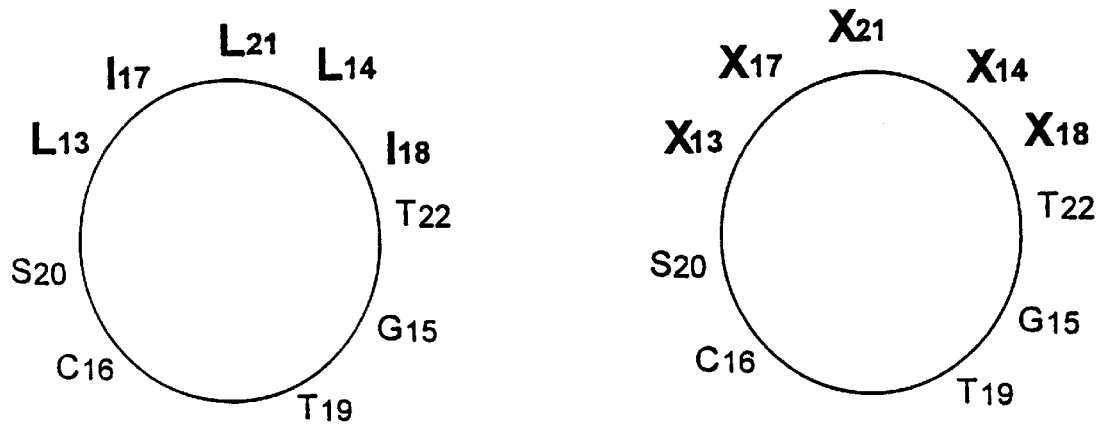
FIG. 1. Helical wheel representations of α-helix 0 (residues 13–21) of HCV protease. Residues in bold font are solvent exposed. (Top) Amino-acid sequence of wildtype α-helix 0; (Left) wild-type α-helix 0; (Right) Amino-acid substitutions in the α-helix 0 variants (X=His, Lys, Glu, Gln, Asp, or Asn) (see Experiments 3 and 4).
Figure 2:
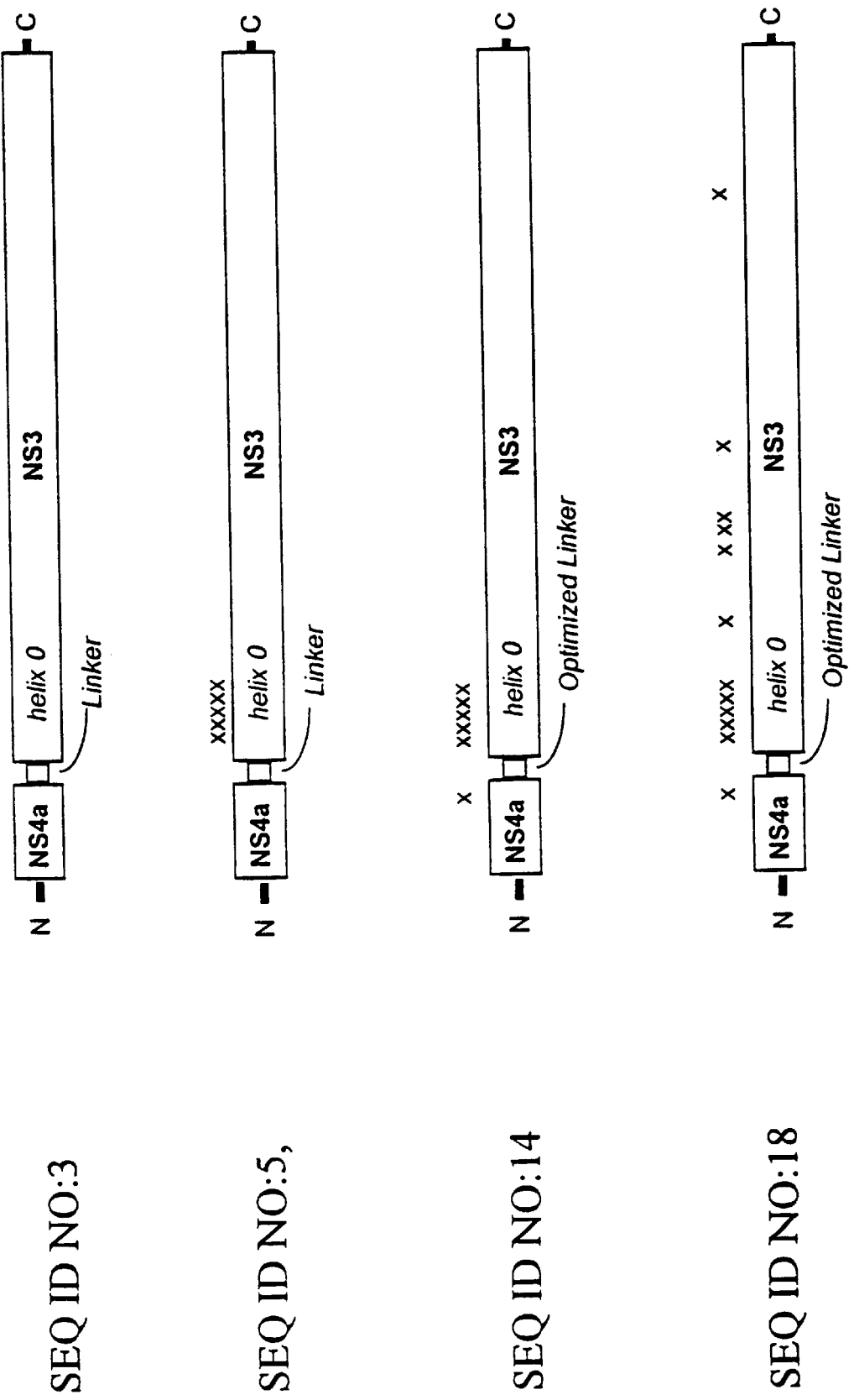
FIG. 2. Diagram of construction of modified HCV NS4a–NS3 fusion proteases. NS4a (residues 21–31) are fused to the N-terminus of NS3 in these diagrams by way of a linker. "X" denotes a sequence change relative to SEQ ID NO:3. "N" and "C" denote the N- and C-termini of the constructs, respectively.
Figure 3:
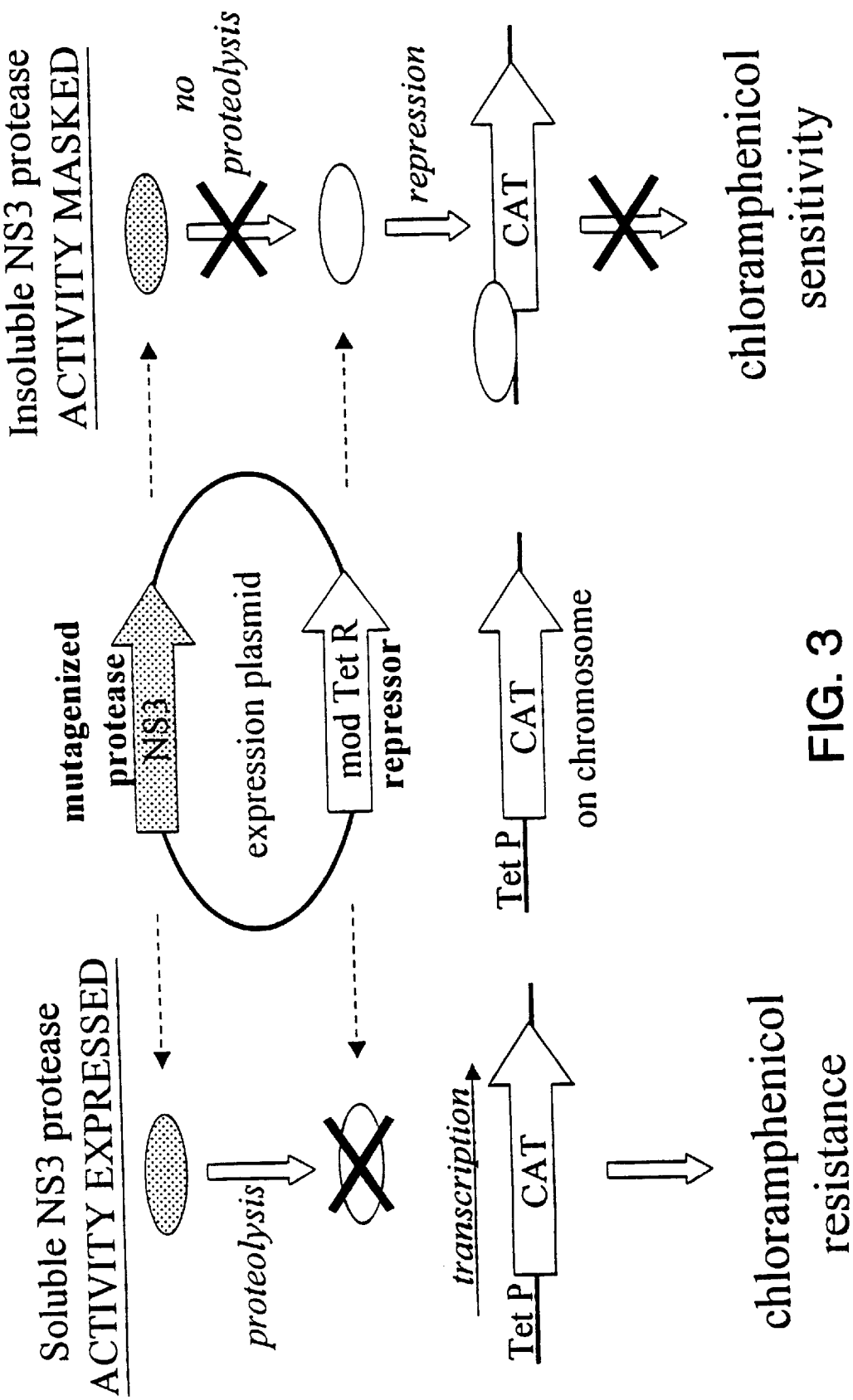
FIG. 3. Diagram of bacterial selection scheme for obtaining soluble HCV protease mutants. See Example 4 for a detailed description of the system. (Center) expression plasmid (expressing HCV NS4a–NS3 fusion protease and modified Tet repressor) and chromosomally encoded Tet promoter-CAT (chloramphenicol acetyl transferase) gene fusion; (Right) case if NS3 protease is insoluble (activity masked by insolubility of the protease resulting in chloramphenicol-sensitive bacteria); (Left) case if NS3 protease is soluble (protease is active resulting in chloramphenicol-resistant bacteria).

The following definitions are provided to more clearly delineate what is contemplated in this invention.

"HCV" refers to the hepatitis C virus.

"HCV NS3" refers to the protein fragment of the HCV polyprotein from any wild type strain of HCV that corresponds to residues 1027–1657 of the HCV polyprotein (as defined in Choo et al *Proceedings of the National Academy of Sciences USA* 88, 2451–2455). The numbering convention for HCV NS3 throughout this application starts with residue 1 corresponding to residue 1027 of the HCV polyprotein, which is the first amino-acid residue of the mature processed NS3 protein fragment. HCV NS3 has portions which confer protease activity, helicase activity, and ATPase activity.

"HCV NS3 protease" refers to any portion of the wild type HCV NS3 that has protease activity, not restricted to, but commonly associated with, HCV NS3 protease domain; or any wild type peptide that exhibits the protease activity associated with HCV NS3.

"HCV NS3 protease domain" refers to the portion of wild type HCV NS3 that confers protease activity, usually encompassing HCV NS3 residues 1–181, but sometimes differing by the inclusion or deletion of residues at either the N- or C-terminus.

"Modified HCV NS3 protease" refers to a peptide or protein whose sequence is an alteration from a wild-type HCV NS3 protease sequence and that exhibits the protease activity of HCV NS3 protease. Such modifications include, but are not limited to, naturally-occurring amino acid substitutions, non-naturally-occurring amino acid substitutions, conservative amino acid substitutions, amino acid insertions, amino acid deletions, and amino acid additions. Non-sequence modifications, including changes in acetylation, methylation, phosphorylation, carboxylation, or glycosylation, are also included in the definition of modified.

"HCV NS4a" refers to the protease-stimulating protein fragment of the HCV polyprotein from any wild type strain of HCV that corresponds to residues 1658–1712 of the HCV polyprotein (as defined in Choo et al. *Procedings of the National Academy of Sciences USA* 88, 2451–2455 [1991]), any fragment thereof that exhibits protease-stimulating activity, or any wild type peptide that exhibits the protease-stimulating activity associated with residues 1658–1712 of the HCV polyprotein. Full-length HCV NS4a particularly refers to residues 1–58, which correspond to residues 1658–1712 of the polyprotein. The numbering convention throughout this invention for HCV NS4a starts with residue 1 corresponding to residue 1658 of the HCV polyprotein (same as the first residue of the mature processed HCV NS4a fragment).

"Modified HCV NS4a" refers to a peptide or protein whose sequence is an alteration from a wild-type HCV NS4a sequence and that exhibits the protease-stimulating activity of HCV NS4a. Such modifications include, but are not limited to, naturally-occurring amino acid substitutions, non-naturally-occurring amino acid substitutions, conservative amino acid substitutions, amino acid insertions, amino acid deletions, and amino acid additions. Non-sequence modifications, including changes in acetylation, methylation, phosphorylation, carboxylation, or glycosylation, are also included in the definition of modified.

"Modified HCV NS4a–NS3 fusion protease" refers to a modified HCV NS3 protease fused to a HCV NS4a or modified HCV NS4a. A modified HCV NS4a–NS3 fusion protease may include an optimized linker sequence.

"Modified forms of HCV NS3 protease" refers to the totality of the invention described herein and encompasses modified HCV NS3 proteases, modified HCV NS4a–NS3 fusion proteases, or both.

"Naturally-occurring amino acid" refers to any of the 20 standard L-acids that occur in a referred-to position in any wild type HCV NS3 protease or wild type HCV NS4a.

"Non-naturally-occurring amino acid" refers to any of the 20 standard L-amino acids that do not occur in a referred-to position in any wild type HCV NS3 protease or wild type HCV NS4a, D-amino acids, and synthetic amino acids such as β or γ amino acids.

"Conservative amino acid substitution" refers to the substitution of one amino acid for another with similar characteristics, e.g., substitutions within the following groups: valine and glycine; glycine and alanine; valine and isoleucine and leucine; aspartic acid and glutamic acid; asparagine and glutamine; serine and threonine; lysine and arginine; and phenylalanine and tyrosine. Other conservative amino acid substitutions can be taken from the table below.

TABLE 1

Conservative amino acid replacements

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met, Ile, D-Ile, |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

"Hydrophobic amino acid" refers to amino acid residues whose side chains are relatively non-polar, including, but not limited to, alanine, phenylalanine, isoleucine, leucine, methionine, proline, valine, and tryptophan.

"Hydrophilic amino acid" refers to amino acid residues whose sidechains are relatively polar, including, but not limited to, aspartate, glutamate, lysine, asparagine. glutamine, arginine, serine, threonine, histidine and tyrosine.

"α-helix 0" refers to the sequence consisting of HCV NS3 residues $Leu_{13}$ through $Leu_{21}$ that takes on an alpha-helical structure when HCV NS3 protease is complexed with a HCV NS4a segment (as in Kim et al, Cell 87, 343–355 [1996] or Yan et al., Protein Science 7, 837–847 [1998]).

"Linker" refers to, in a modified NS4a–NS3 or NS3–NS4a fusion protease, a polypeptide sequence that joins the HCV NS4a sequence with the HCV NS3 sequence.

"Optimized linker" refers to, in a modified NS4a–NS3 fusion protease, a linker sequence that joins the NS4a and NS3 sequences such that the resulting fusion protein has enhanced stability and solubility characteristics relative to a non-optimized linker.

"Zinc-binding cysteine residues" refer to the naturally-occurring cysteine residues $Cys_{97}$, $Cys_{99}$, and Cys145 in HCV NS3.

"Non-zinc-binding cysteine residues" refer to the naturally-occurring cysteine residues $Cys_{47}$, $Cys_{52}$, and $Cys_{159}$ in HCV NS3.

DETAILED DESCRIPTION OF THE INVENTION

The benefit of this invention is that the modified forms of HCV NS3 protease retain full activity, yet are highly amenable to biochemical experimentation because of their highly soluble (>30 mg/ml) and non-aggregating nature under detergent-free conditions. In contrast, wild-type forms of the HCV NS3 protease (domain) require detergents for solubilization. Because the modified forms of HCV NS3 protease of the invention exhibit very high degrees of solubility in the absence of detergents, they are well suited for NMR and X-ray crystallographic structure determination of HCV NS3 protease complexed with inhibitors, facilitating iterative structure-based drug design efforts with this pharmacologically important enzyme. Their solubility without the use of detergents also makes them very useful in screening assays for inhibitors.

As previously noted, one aspect of the invention is a modified HCV NS3 protease comprising at least one substitution in HCV NS3 protease of a hydrophobic α-helix 0 amino acid residue to a hydrophilic amino acid residue.

Another aspect of the invention is a modified HCV NS4a–NS3 fusion protease comprising a modified HCV NS3 protease fused to a HCV NS4a or modified HCV NS4a.

Various combinations in which hydrophobic amino acids are substituted to hydrophilic amino acids in the α-helix 0 are described elsewhere in the specification and in the claims. In a preferred embodiment, the hydrophobic α-helix 0 amino acid residues are selected from the group consisting of $Leu_{13}$, $Leu_{14}$, $Ile_{17}$, $Ile_{18}$, and $Leu_{21}$. In a more preferred embodiment, $Leu_{13}$ is substituted to glutamic acid, $Leu_{14}$ is substituted to glutamic acid, $Ile_{17}$ is substituted to glutamine, $Ile_{18}$ is substituted to glutamic acid, and $Leu_{21}$ is substituted to glutamine. (This is helix 0–1 in FIG. 11, SEQ ID NO: 6.) In another more preferred embodiment, $Leu_{13}$ is substituted to glutamic acid, $Leu_{14}$ is substituted to glutamine, $Ile_{17}$ is substituted to glutamine, $Ile_{18}$ is substituted to lysine, and $Leu_{21}$ is substituted to histidine. (This is helix 0–7 in FIG. 11, SEQ ID NO: 9.)

In another preferred embodiment of the invention, the modified HCV NS3 protease further comprises at least one substitution of a hydrophobic amino acid residue not in the α-helix 0 to a hydrophilic amino acid residue.

In an additional preferred embodiment, the modified HCV NS3 protease further comprises at least one substitution of a non-zinc-binding cysteine residue to a non-cysteine amino acid residue.

In a preferred embodiment, the HCV NS3 protease that is altered comprises approximately residues 1–1 81 of HCV NS3.

In a preferred embodiment of an aspect of the invention that is a modified HCV NS4a–NS3 fusion protease, the HCV NS4a that is altered or unaltered comprises approximately residues 21–31 of full-length HCV NS4a.

In an aspect of the invention that is a modified HCV NS4a–NS3 fusion protease, a preferred embodiment further comprises a linker comprising an optimized linker sequence. In a more preferred embodiment, the NS4a is linked to the amino terminus of the NS3. In a most preferred embodiment, the optimized turn sequence is Ser-Gly-Asp-Thr where Ser corresponds to NS4a residue $Ser_{32}$ and Thr corresponds to NS3 residue $Thr_4$.

In a preferred embodiment of an aspect of the invention that is a modified HCV NS4a–NS3 fusion protease, the modified HCV NS4a further comprises at least one substitution of a hydrophobic amino acid residue to a hydrophilic amino acid residue. In a most preferred embodiment, residue 30 is substituted to asparagine.

The invention also includes isolated nucleic acid molecules encoding the proteins of the present invention, vectors comprising said nucleic acid molecule, and host cells comprising said vectors. E. coli cells harboringing plasmids containing certain nucleic acid molecules of the present invention were deposited on Jan. 7, 1999 with the American Type Culture Collection (ATCC), 10801 University Blvd., Manassas, Va., 200110 USA, and have ATCC accession numbers 204070 and 204071.

The invention also includes methods of making proteins of the present invention using host cells of the present invention.

The present invention exhibits distinct differences from and improvements over the prior art. In contrast to the published works documenting attempts to solubilize the HCV NS3 protease by relying solely on the fusion of solubilizing tags or protein fusion partners to the protease (i.e Kim et al. 1996; Yan et al., 1998; Taremi et al., 1998), the present invention changes amino-acid residues within the HCV NS3 protease coding region itself, resulting in what is referred to herein as modified forms of the HCV NS3 protease. These modified forms retain full enzymatic activity.

The present invention provides solubility of greater than 30 mg/ml—the highest reported level of detergent-free solubility for an HCV NS3 protease of any kind (wild type or engineered in any way).

Applicants have used the present invention to collect high quality NMR spectra. Presented herein are high quality NMR spectra of a modified form of HCV NS3 protease and of a modified form of HCV NS3 protease:inhibitor complex. These are the first reported instances of high quality NMR spectra of an HCV protease (wild type or engineered in any way) alone or in complex with an inhibitor.

Applicants herein present a modified form of HCV NS3 protease:inhibitor complex determined by X-ray crystallography and demonstrate that the proteins of the present invention can rapidly produce high quality co-crystals with protease inhibitors. This is the first reported instance of X-ray crystallography showing an HCV protease (wild type or engineered in any way) complexed with an inhibitor. The proteins of this invention are especially useful because of their ability to produce high quality co-crystals with protease inhibitors. Structure-based drug design with a protein is often limited by it's ability to form diffraction-grade co-crystals with inhibitors in a timely manner. A protein, such as that of the present invention, that can be co-crystallized quickly facilitates the iterative process of structure-based design work.

The modified forms of HCV NS3 protease of the present invention are also useful for screening for small molecules inhibitors of HCV NS3. Proteins of the present invention can be prepared in the absence of detergents, allowing for the identification of compound inhibitors that would otherwise be undetectable if screened in the presence of detergents. The modified HCV NS3 protease in the non-fusion form can also be used to study whether a compound interferes with the binding of NS4a to NS3.

The general strategy used to obtain these soluble modified HCV NS3 protease variants was to sequentially target key regions of the protein that might be important for protein solubility, mutagenize these targeted regions in a semi-random manner, and either select or screen for bacterial clones expressing protein variants that exhibited higher degrees of solubility. The steps used to make some of the preferred embodiments of the invention are outlined in the Examples. Over the course of the Examples, a progressively higher degree of amino-acid residue substitution (relative to the starting wild-type sequence) was generated until the production of modified forms of HCV NS3 protease that exhibited high levels of solubility with low levels of aggregation was achieved. Many different hydrophobic-to-hydrophilic HCV NS3 protease surface residue substitutions (naturally-occurring and non-naturally-occurring) were combined with different NS4a–NS3 fusion linker sequences, and these protease mutants were either selected or screened to find modified proteins that exhibited the desired solubility characteristics. Some completely conserved hydrophobic residue positions in the α-helix 0 were targeted for mutagenesis because they made up a particularly extensive hydrophobic patch on the surface of HCV NS3 protease. Other HCV NS3 protease hydrophobic surface residues were also mutagenized; particularly good candidates were residues whose position was variable among the HCV NS3 sequences from other wild type HCV isolates. These and other substitutions are documented and included in the claims.

The following paragraphs describe in greater detail the invention claimed and ways of making it. While the order of the paragraphs follows the experimental process used, one of skill in the art can figure out ways to make the invention claimed in which the steps are done in different orders and/or steps are omitted.

Any HCV NS3 protease and HCV NS4a sequences can be used as a starting point for the modifications. Here, a cloned HCV isolate sequence was used as a starting point for the mutagenesis experiments (Example 1, FIG. 9, SEQ ID NO: 2]. The expression system used features a synthetic gene in which all codons have been optimized for high-level expression in E. coli. While this may explain the high levels of expression observed for the resulting constructs, it is not essential to the invention and any nucleotide sequence encoding an HCV NS3 protease (using the standard genetic code) could be used to express these proteins. HCV NS3 protease includes any fragment of wild type HCV NS3 that exhibits protease activity or any wild type peptide that exhibits the protease activity associated with wild type HCV NS3 (as defined in the Definitions section). It is also not essential that the modified forms of HCV NS3 protease described here be expressed in E. coli. Any in vivo expression host (bacterial, insect, plant, mammalian, other) could be used to express these modified forms of HCV NS3 protease. Also, in-vitro production of these variants is possible. The present invention includes modified forms of HCV NS3 protease produced by any means.

The invention includes the use of HCV NS4a. See the Definitions section for the definition of HCV NS4a. In Example 2, the NS4a sequence comprising residues 21–31 ($G_{21}$ $S_{22}$ $V_{23}$ $V_{24}$ $I_{25}$ $V_{26}$ $G_{27}$ $R_{28}$ $I_{29}$ $V_{30}$ $L_{31}$) of full-length NS4a (SEQ ID NO: 26) was fused to the N-terminus of the HCV NS3 protease. The linker sequence in this experiment was the simple dipeptide sequence asparagine-glycine. A variety of other linkers could be used, and one of ordinary skill in the art would be able to choose other appropriate linkers. The NS4a could also be fused to the C-terminus of the NS3. As has been demonstrated (Lin et al., 1995; Tomei et al., 1995; Shimizu et al., 1996), a NS4a peptide including residues 21–31 increases the activity of the HCV NS3 protease in vitro. The linker described in Example 2 was initially used. However, better results (in terms of expression and solubility) were obtained from the optimized linker constructs resulting from the experiments described in Example 5. While others have very recently published other NS4a–NS3 linkers (Taremi et al., 1998; Pasquo et al., 1998), the optimized linkers documented in this invention (in combination with the other mutations described here) confer unprecedented levels of protease solubility.

The first α-helix of HCV NS3, known as α-helix 0, has an extremely hydrophobic solvent-exposed surface (Yan et al, 1998), and applicants believed that this could be a contributor to the insoluble character of preparations of wild type HCV NS3 protease (such as SEQ ID NO: 1 in FIG. 9) and unmodified HCV NS4a–NS3 fusion protein (such as SEQ ID NO: 3 in FIG. 10). Therefore, the targeted/semi-random mutagenesis method was applied in an effort to change the hydrophobic solvent-exposed residues of α-helix 0 to more hydrophilic residue types (see Examples 3 and 4). Currently, all known strains of HCV have five hydrophobic solvent-exposed residues in α-helix 0 ($L_{13}$, $L_{14}$, $I_{17}$, $I_{18}$, $L_{21}$), and, according to this invention, these could be changed alone or in any combination. Applicants chose to mutate all five in tandem. Changing other solvent-exposed hydrophobic residues in α-helix 0 in strains currently unknown is also encompassed by this invention, as is changing hydrophobic residues in α-helix 0 that arc not solvent-exposed. Although applicants demonstrate changes to the α-helix 0 of a HCV NS4a–NS3 fusion protease, the unfused HCV NS3 protease could also undergo such changes and a such modified HCV NS3 protease is encompassed by this invention.

A simple method of isolating a soluble modified form of HCV NS3 protease from a large library of candidate mutants is to simply screen for the presence of modified HCV NS4a–NS3 fusion protein variants in the cleared supernatants of induced transformants by SDS-PAGE analysis, similar to the analysis depicted in FIG. 4. This method is laborious and inherently low-throughput. Another, much more powerful high-throughput method is to have a system where the most soluble modified forms of HCV NS3 protease are selected from among all the other clones in the library. Applicants have used such a selection scheme to select for more soluble modified forms of HCV NS3 protease. (See Example 4 and FIG. 3.) What applicants describe is a specific application of a general method for selecting for soluble (or active) variants of proteases. This scheme can be used to screen for solubility or activity of any of the modified forms of HCV NS3 protease encompassed by this invention.

The modified HCV NS4a–NS3 fusion proteases having α-helix 0 mutations only (described in Example 4) retained full enzymatic activity and were considerably more soluble than the non-mutated NS4a–NS3 fusion (see FIG. 4, compare lanes 3 and 5). These mutants are useful for experiments where the protein concentration can be kept relatively low, such as enzyme assays. Also, these mutants allow the bacterial selection system (FIG. 3) to be used as a screening system for HCV protease inhibitors. (Inhibitors will cause a decrease in the growth of these induced bacteria in chloramphenicol media.) Similarly, the modified HCV NS3 proteases that are not fusions could be used in enzyme assays and to screen for inhibitors. However, the modified HCV NS4a–NS3 fusion proteases having only α-helix 0 mutations still had a tendency to aggregate at the high protein concentrations required for protein NMR (see FIG. 5, panel A). One concern was that the NS4a and NS3 segments were not fused optimally. Therefore, work was done to optimize the linker sequence connecting the NS4a and NS3 segments.

Many different methods can be used to optimize a linker sequence. In general, the goal is to successfully connect two protein segments using a polypeptide linker so that the relative spatial positioning of the two segments is maintained with minimal stress and perturbation to the structure. Another important aspect is that the linker should ideally not be highly flexible, as this might tend to destabilize the protein. In this case, because the desired relative structural positioning of the NS4a and NS3 segments was known, a structure-based approach was taken to find an optimal linking sequence. As described in Example 5, the structural information in the Brookhaven Protein Data Base (PDB) was mined to find short turn sequences that successfully linked two beta-strands that were structurally similar to the NS4a (residues) and NS3 (residues) segments as seen in the published X-ray structure of the HCV NS3 protease/NS4a peptide complex. Coordinates from Protein Database file 1JXP.pdb (Yan et al., *Protein Science* 7, 837–847 [1998]) were used for this purpose. In addition, the sequential proximity of a surface-exposed hydrophobic residue within the NS4a segment ($Val_{30}$) provided the opportunity to test the effect of mutation of this residue while trying the different linker sequences.

One optimal linker sequence among those tested conferred high levels of expression and solubility. This optimized linker sequence in combination with the wild-type α-helix 0 (SEQ ID NO: 24 in FIG. 18) does not confer solubility to the protease while the optimized turn in combination with a modified α-helix 0 (SEQ ID NO: 14 in FIG. 13) does (FIG. 4, compare lanes 7 & 9). Overall, the quality of the NMR spectra obtained with the modified α-helix 0/optimized linker form of the protease (SEQ ID NO: 14—FIG. 5, panel B) was superior to that obtained with the modified α-helix 0/non-optimized linker form of the protease (SEQ ID NO: 12—FIG. 5, panel A), indicating a more soluble and less-aggregating form of the protease.

The effect of additional solvent-exposed hydrophobic-to-hydrophilic amino-acid substitutions was explored by changing certain surface residues in SEQ ID NO: 14, resulting in SEQ ID NO: 16 (see Example 6). The residues were chosen by aligning HCV NS3 protease sequences from published sequences of wild type HCV isolates and looking for naturally-occurring hydrophobic-to-hydrophilic amino-acid substitutions at residue positions that are solvent exposed in published NS3 protease structures. The combination of three of these naturally-occurring substitutions (A40T, 172T, P86Q) were found to have a solubility enhancing effect (SEQ ID NO: 16 in FIG. 14). In addition, three of the four non-zinc binding cysteine residues were targeted for amino-acid substitutions (SEQ ID NO: 18 in FIG. 15). Other sequences generated by this process can also yield useful results. Two variants of the Helix0–7 sequence variant (see FIG. 11—SEQ ID NO. 9) was substituted for the Helix0–1 sequence (see FIG. 11—SEQ ID NO. 6) to generate SEQ ID NOS: 20 and 22. These modified HCV NS4a–NS3 fusion protease variants were also highly soluble.

In order to demonstrate the usefulness of the resulting protease variants for structural studies of the protease and protease:inhibitor complexes, the modified HCV NS3 protease encoded by SEQ ID NO: 18 was characterized by multi-dimensional NMR spectroscopy (Examples 8 and 9) and X-ray crystallography (Example 10).

In Example 8, NMR spectroscopy of the apo-form of the protease was used to generate sequential backbone assignments and sidechain NMR assignments. These assignments include the catalytic triad residues $His_{57}$, $Asp_{81}$, and $Ser_{139}$ and the residues spatially near to them, indicating that spectra of the apo-form of the protein is a useful tool for analyzing of the effect of addition of potential NS3 protease inhibitors using chemical shift perturbation mapping. As shown in Example 9, addition of a published peptidic HCV protease inhibitor causes many chemical shift perturbations for residues in the $^1H$-$^{15}N$ HSQC NMR spectrum of the protease, including the active site residues. This is the first publication of high quality NMR spectra of HCV NS3 protease and of a HCV NS3 protease:inhibitor complex. As demonstrated here, the modified protease yields high quality NMR spectra that can be used to identify compounds that bind to the protease. One can use this chemical-shift mapping technique to identify novel compounds that bind to the protease by collecting a series of spectra in which different compounds have been mixed with the protease.

Example 10 demonstrates that the modified HCV NS3 protease encoded by SEQ ID NO: 18 can be co-crystallized with a published HCV protease inhibitor overnight, resulting in high quality crystals that diffract to 2 Å. This is the first publication of a HCV NS3 protease:inhibitor complex solved by X-ray crystallography and demonstrates that proteins produced by application of this invention can rapidly produce high quality co-crystals with protease inhibitors. In addition, the high resolution structure verifies that the NS4a–NS3 fusion construct produces the relative structural positioning of the NS4a–NS3 polypeptide segments as designed.

The nucleic acid molecules of the present invention can be made by one of ordinary skill in the art using standard knowledge of codon usage and molecular biology techniques that can be found in, for example, "Molecular Cloning, A Laboratory Manual" ($2^{nd}$ edition, Sambrook, Fritch and Maniatis 1989, Cold Spring Harbor Press).

The vectors of the present invention which comprise nucleic acids of the present invention can be made using any suitable vector as determined by one of ordinary skill in the art. Such vectors include, but are not limited to, vectors such as pBR322 and expression vectors such as pET series (Novagen). The vectors of the present invention can be produced using standard molecular biology techniques as found in, for example, "Molecular Cloning, A Laboratory Manual" ($2^{nd}$ edition, Sambrook, Fritch and Maniatis 1989, Cold Spring Harbor Press).

Any suitable host cell can be used, such as bacterium, insect, plant, mammal or other. Conditions for expression and recovery of the proteins can be determined by one of ordinary skill in the art using techniques found in, for example, Protein Expression in Mammalian and Insect Cell Systems, S. Geisse and H. P. Kocher in *Methods in Enzymology*, Vol. 306 (1999), p. 19–42.

All references cited in this specification are incorporated herein by reference.

EXAMPLES

The following Examples explain how to make and use certain embodiments of the invention. From these Examples, the Detailed Description of the Invention, and the references cited therein, one of ordinary skill in the art can readily discern how to make these and other embodiments of the invention. The Examples are not meant to limit the scope of the invention; the scope of the invention is delineated by the claims.

In the following Examples, the standard residue numbering for HCV NS3 protease is used (as outlined in the Definitions). In cases where sequences are added to the N-terminus, the NS3 numbering remains the same, sometimes resulting in negative numbering for the additional N-terminal residues. All presented protein sequences are aligned in FIG. 6.

Example 1

Parental HCV Protease DNA Sequence

The HCV NS3-encoding DNA used as a basis for all the subsequent modifications is a synthetic gene coding for the HCV protease (residues 1–181) shown in SEQ ID NO: 2 (FIG. 9). Residues 1–181 per Choo et al. correspond to Residues 2–182 in SEQ ID NO: 1 and in FIG. 9. Residues 1–181 comprise the portion of the HCV NS3 gene product that exhibits protease activity. Longer fragments of the HCV NS3 protein could be used. The synthetic gene was constructed so that all codons were optimized for high level expression in *E. coli*. The protein-coding sequence of this construct is shown in SEQ ED NO: 1 (FIG. 9). This HCV protease protein is produced at a high level when expressed from vector pET24a (Novagen) in *E. coli* strain BL21(DE3) (Novagen), but upon fractionation of the extract the protease is in the insoluble fraction (data not shown).

Example 2

Fusion of Wild Type NS4a to Parental NS3 with a Linker

A plasmid was constructed that encoded the following portion of the full-length HCV NS4a sequence: NS4a residues 21–31; $G_{21}$ $S_{22}$ $V_{23}$ $V_{24}$ $I_{25}$ $V_{26}$ $G_{27}$ $R_2V_{30}$ $L_{31}$ (SEQ ID NO: 26). This portion of the NS4a sequence was fused to the amino-terminus of the HCV NS3 protease sequence (NS3 HCV protease sequence 5–183). The fusion was constructed so that the NS4a segment was fused to the NS3 segment by means of a linker (Asn Gly, aka NG), yielding the protein sequence . . . GSVVIVGRIVLNGAYAQQ . . . at the NS4a–NS3 fusion (see Seq ID NO:3 in FIG. 10).

The expression plasmid for the NS4a-linker-NS3 fusion protease was constructed by a three-way ligation of the following three DNA preparations:

1) The vector for the expression plasmid was a modified form of pET28a (Novagen), where pET28a plasmid DNA had been double-digested with XhoI and SalI, and subsequently ligated, destroying both sites in the vector. The resulting modified vector (mpET28a) was double digested with NdeI and EcoRI.

2) Two synthetic 5'-phosphorylated oligonucleotides (coding for the NS4a and linker segments) were annealed, creating NdeI and XhoI sticky ends.

5'-TATGAAAAAAAAAGGATCCGTTGT-
   TATCGTCGGCCGTATAGTACTGAACGGT-
   GCTTACGCTCGCAGAC-3'

5'-TCGAGTCTGCTGAGCGTAAGCACCGT-
   TCAGTACTATACGGCCGACGATAA-
   CAACGGATCCTTTTTTTTTCA-3'

3) The NS3-coding DNA from Seq 1 NO: 1 was PCR amplified with the following oligonucleotides which created a silent mutation encoding a XhoI site. The resulting PCR fragment was digested with XhoI and EcoRI.

5'-CAGCAGACTCGAGGTCTGC-3'

5'-GCACGAATTCACGGGGAACGCATGG-3'

The plasmid product of this three-way ligation codes for a NS4a–NS3 fusion protein (see Seq ID NO:3 in FIG. 10; SEQ ID NO: 3). This fusion protein is produced at a high level when expressed in E. coli, but upon fractionation of the extract the fusion protein is in the insoluble fraction (see FIG. 4, lanes 2 & 3).

Example 3

Figure 4:
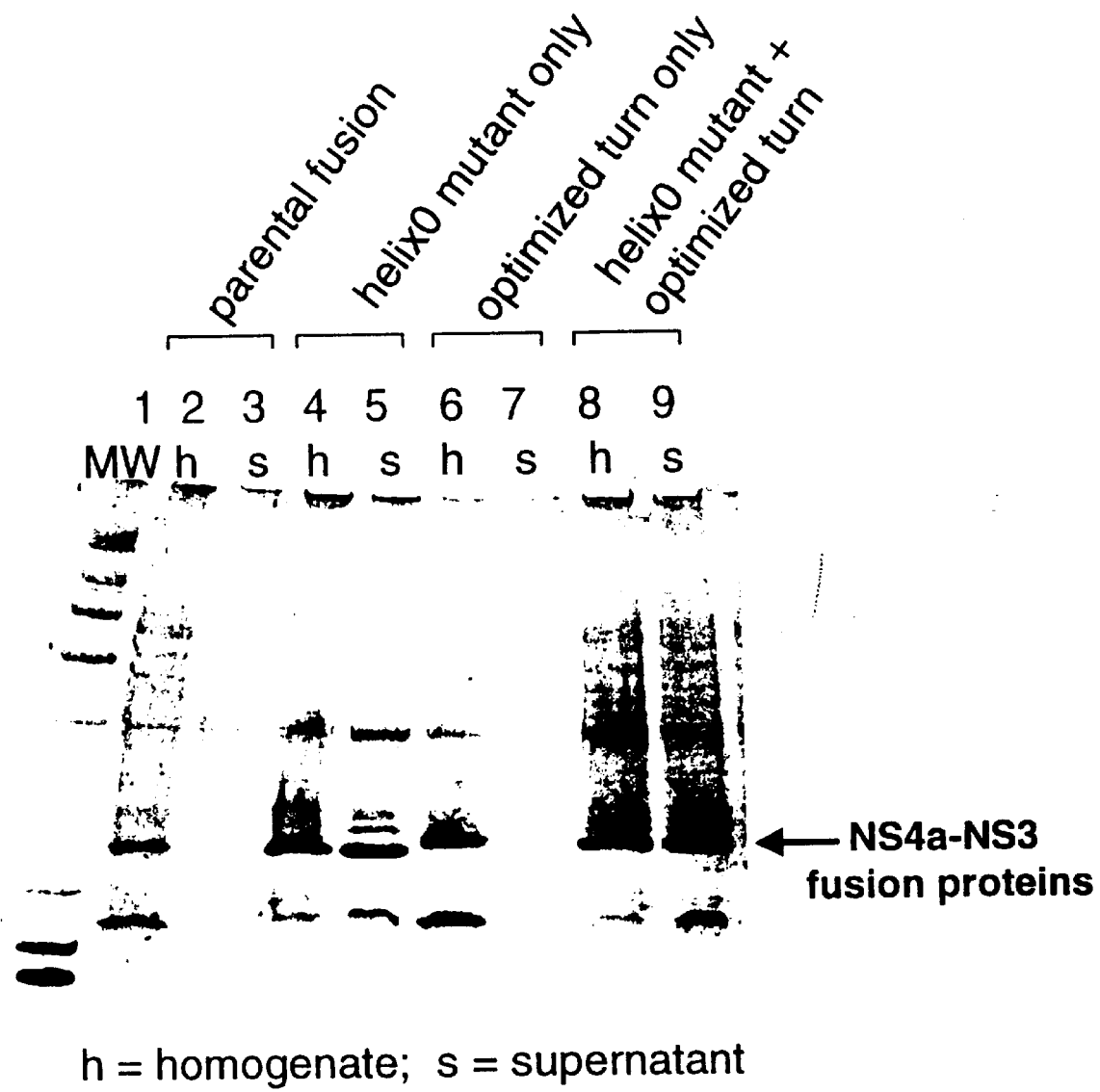
FIG. 4. SDS-PAGE analysis of expression of various HCV NS4a–NS3 fusion protein constructs. Plasmid containing cells were grown to $OD_{600}$–0.7 and 10 ml cultures were induced with 0.25 mM IPTG for 20 hours at 20 degrees C. Cells were harvested by centrifugation (1500 rfc) in a tabletop microfuge and cell pellets were resuspended in 1ml of 25 mM Na—phosphate buffer,pH 7.5; 0.5M NaCl, 2 mM DTT, 10:M ZnCl, 10 mM MgCl, 10:g/ml DNAse and sonicated twice for 1 min at power 5 in pulse mode. The homogenates were spun down in tabletop microfuge at max speed (20800 rfc) for 20 min. Homogenates and supernatants were analyzed on 10–20% SDS-PAGE pre-cast gels (Bio-Rad). Lane 1, molecular weight standards. The following samples are in pairs of homogenate and supernatant, respectively: Lanes 2 & 3, parental fusion (SEQ ID NO:3); Lanes 4 & 5, helix0–1 mutations only (SEQ ID NO:12); Lanes 6 & 7, optimized linker only (SEQ ID NO:24); Lanes 8 & 9, helix0–1 mutations with optimized linker (SEQ ID NO: 14).

Generation of a Large Library of Modified HCV NS4a–NS3 Fusion Proteases in which the Hydrophobic Solvent-exposed Residues of α-helix 0 are Replaced with Hydrophilic Residues The HCV NS3 protease sequence generated in Example 2 (Seq ID NO:3) was PCR amplified and moved into another expression vector as a NcoI-SalI fragment. This modified expression vector (depicted in FIG. 3) is derived from pET21 (Novagen) and includes a modified Tet repressor in which a HCV NS3 protease site has been inserted. The vector was cut with NcoI and XhoI, and ligation with the NcoI-SalI fragment resulted in the destruction of the XhoI site within the pET21-derived multiple cloning site in this plasmid vector.

The five hydrophobic solvent-exposed residues in α-helix 0 ($L_{13}$, $L_{14}$, $I_{17}$, $I_{18}$, $L_{21}$) were singled out for targeted semi-random mutagenesis using the biased codon method (Kamtekar et al., Science 262, p1680–1685 [1993]). In this method, a "VAV" codon (V=G, C, or A) encodes a mixture of six possible codons all coding for hydrophilic residue types (His, Glu, Gln, Asp, Asn, or Lys).

The targeted semi-random mutagenesis was carried out by using this oligonucleotide sequence as the 5' primer for PCR amplification of the HCV NS3 protease sequence:

```
    XhoI
Gln Thr Arg Gly *** *** Gly Cys *** *** Thr Ser *** Thr Gly Arg Asp 9  10  11  12  13  14  15  16  17  18  19  20  21  22  23  24  25

CAG ACT CGA GGT VAV VAV GGT TGC VAV VAV ACC TCC VAV ACC GGT CGT GAC
``` where V=(G or C or A)

A 3' primer was used to prime at a site downstream of the NS3 protease stop codon and EcoRI site. The PCR products were digested with Xhol and EcoRi and ligated into the XhoI-EcoRI cleaved HCV NS4a–NS3 fusion protease expression vector described at the beginning of this Example.

In this way, a library of 7776(=$6^5$) potential unique modified HCV NS4a–NS3 fusion proteases with different mutant hydrophilic α-helix 0 sequences was generated. Portions of the ligation mixture were electroporated into *E. coli* strain MC1061 (ATCC 5338). Over 50,000 transformants were pooled and plasmid DNA was isolated.

The plasmid used as a vector for the construction of this library is diagrammed in FIG. 3 and is relevant to the mutant selection experiments described in Example 4. When another selection or screening method is used (such as screening by SDS PAGE analysis of homogenates of induced transformants [as in FIG. 4]), other plasmid vectors would be suitable.

Example 4

Bacterial Selection of Soluble Modified HCV NS4a–NS3 Fusion Proteases

The bacterial selection system is diagramed in FIG. 3. The system features a plasmid encoding a mutagenized HCV protease gene (in this case, the modified HCV NS4a–NS3 fusion proteases with the α-helix 0 mutations) as well as a gene encoding a modified Tet repressor. The modification of the Tet repressor is the introduction of a HCV NS3 protease cleavage site within a solvent-exposed loop of the Tet repressor protein. The strain carrying this plasmid also has a chromosomally-encoded chloramphenicol acetylase transferase gene (CAT—conferring chloramphenicol resistance) under the control of the Tet promoter. After induction of the modified HCV NS4a–NS3 fusion protease by IPTG (under lac-T7 control), the strain becomes either chloramphenicol resistant ($Cm^R$) if the protease activity is present (cleavage of the modified Tet repressor allowing expression of CAT) or remains chloramphenicol sensitive ($Cm^S$) if the fusion protease activity is not present (no cleavage of the modified Tet repressor and therefore there is repression of CAT).

In this case, the expressed wildtype HCV protease is inherently active, however the activity is masked by the insoluble character of the expressed protease, resulting in a $Cm^S$ phenotype. If among the pool of mutagenized transformants a more soluble active mutant protease is expressed, the inherent activity of the protease is unmasked by the soluble nature of the mutant enzyme and the cells harboring this mutant protease become $Cm^R$.

Expression of the parental HCV NS4a–NS3 fusion protease (SEQ ID NO: 3) in this section system system yielded *E. coli* cells that grew only very slowly on agar plates with 1 μg/ml chloramphenicol. The library of α-helix 0 mutants (described in Example 3) was transformed into the *E. coli* selection strain. Many plasmids encoding α-helix 0 mutagenized modified HCV NS4a–NS3 fusion proteases conferred upon induced transformed *E. coli* cells an enhanced ability to grow on plates with low levels of chloramphenicol (1–3 μg/ml chloramphenicol). However, twelve transformants grew on plates with very high levels of chloramphenicol (30 μg/ml). These highly $Cm^R$ transformants were colony purified and solubilities of the expressed mutant HCV NS4a–NS3 fusion proteases were evaluated by SDS-PAGE analysis (similar to that depicted in FIG. 4). Six of the transformants exhibited more soluble proteases than the others and plasmid DNA was prepared and sequenced. The relevant portions (through the NS3 α-helix 0 segment) of the sequences from these isolates are listed as SEQ ID Nos: 6–11 (see FIG. 11).

As shown in FIG. 4 (lanes 4 & 5), expression of a modified HCV NS4a–NS3 fusion protease with the Helix0–1 sequence (see SEQ ID NO: 6 and SEQ ID NO: 12) produced a protein that was in the soluble fraction while fusion protein with the wild-type α-helix 0 sequence was insoluble (lanes 2 & 3). Similar enhancements in solubility were obtained with the other five sequenced variants.

E. coli cells containing a similar expression system have been deposited with the ATCC and have ATCC accession number 207047. The cells submitted to the ATCC differ from the cells used here in that the ATCC cells have a plasmid containing a CMV protease and the CMV protease cleavage site within the Tet repressor, and in that the CAT gene is on a second plasmid, rather than on the chromosome.

One of ordinary skill in the art could make a cells useful for the present invention from the cells deposited with the ATCC by replacement of the CMV protease sequences with HCV protease sequences and changing the CMV cleavage site coded within the Tet repressor gene to a HCV protease cleavage site. Cells useful for the present invention could have the CAT gene on a second compatible plasmid rather than on the chromosome.

The cells having ATCC accession number 207047 and the bacterial selection system referred to herein are further described in application U.S. Ser. No. 60/115,270, filed on Jan. 8, 1999, and application U.S. Ser. No. 09/478,631, filed on even date herewith, both of which are incorporated herein by reference.

Example 5

Linker Optimization in a Modified HCV NS4a–NS3 Fusion Protease, Including Change in NS4a Structural information from the Protein Data Bank was used to identify structurally characterized proteins that have two β-strands (structurally homologous to residues NS4a residues $G_{27}$-$R_{28}$-$I_{29}$-$V_{30}$-$L_{31}$, and NS3 residues $A_5$-$Y_6$-$A_7$-$Q_8$-$Q_9$) linked by a tight turn (*Searchloop* function in the Insight II program, Molecular Simulations Inc.). Three different turn types were identified (as exemplified by the Brookhaven Protein DataBase (PDB) files 1OPB [residues 45–48], 1LID residues 109–112], and 1EUR [residues 177–184]) and three sets of degenerate double stranded oligonucleotides were synthesized that coded for 8 to 12 variants of each of the three turn types.

Turn oligo #1:

```
                  Asn           Asn           Ser
GlyArgIleIleLeuSerGlyAspThrAlaTyrAlaGlnGlnThr
GGCCGTATCAWCCTGTCCGGTRACACCGCTTACKCTCAGCAGAC
    CATAGTWGGACAGGCCAYTGTGGCGAATGMGAGTCGTCTGAGCT
```

Turn oligo #2:

```
                  Asn           Asn           Ser
GlyArgIleIleLeuSerAspGlyThrAlaTyrAlaGlnGlnThr
GGCCGTATCAWCCTGTCCRACGGTACCGCTTACKCTCAGCAGAC
    CATAGTWGGACAGGYTGCCATGGCGAATGMGAGTCGTCTGAGCT
```

Turn oligo #3:

```
              Asn                            Ser
GlyArgIleIleLeuSerAspGlyGlyIleThrAlaTyrAlaGlnGlnThr
GGCCGTATCAWCCTGTCCGACGGTGGTATCACCGCTTACKCTCAGCAGAC
    CATAGTWGGACAGGCTGCCACCATAGTGGCGAATGMGAGTCGTCTGAGCT
```

Where W=(A,T); K=(G,T); M=(A,C); R=(A,G); Y=(C,T).

These variants (20 possible sequence possibilities in all) were incorporated into an optimized constrict from Example 4 by subcloning the three oligos separately using the EagI and XhoI sites in SEQ ID NO: 13.

In addition to the linker sequence, a single solvent-exposed residue within the NS4a sequence ($Val_{30}$) was allowed to be either isoleucine or asparagine in this series of linker variants. This residue position is always a hydrophobic residue (usually Val or Ile) in wild-type isolates of HCV. Therefore, an Asn substitution at this position would be a non-naturally occurring substitution. In contrast, the residue corresponding to NS3 residue 7 ($Ala_7$) was allowed to be either alanine or serine, but both of these residue-types are present at this position in different wild-type isolates of HCV. It was hypothesized that serine at this solvent-exposed position might confer more solubility because it is more hydrophilic than alanine.

Protease expression levels and solubilities of randomly picked linker variant modified HCV NS4a–NS3 fusion proteases were monitored by SDS-PAGE analysis of the soluble fractions of induced cell lysates (same procedure as outlined in the legend to FIG. 4). One linker variant (resulting from incorporation of a variant of the Turn oligo #1) was clearly better than the rest in tenus of both protein expression levels and solubility. This linker sequence ( . . . $G_{-4}R_{-3}I$-$2N_{-1}L_0S_1G_2D_3T_4A_5Y_6A_7Q_8Q_9T_{10}$. . . ) and the resulting modified HCV NS4a–NS3 fusion protease is shown in SEQ ID NO: 14. It incorporates the asparagine mutation within the NS4a segment (numbered −1 in this fusion construct and numbered 30 in the NS4a sequence) and retains the alanine at NS3 position 7.

FIG. 6 shows an alignment of the protein sequences of SEQ ID Nos: 1, 3, 12, 14, 16, 18, 20, 22 and 24. As seen in FIG. 6, the linker segment of SEQ ID NO: 14 is two residues longer relative to the original linker used in SEQ ID Nos: 3 and 12.

The optimized turn sequence by itself is not sufficient to confer solubility on a NS4a–NS3 fusion. This can be seen in lanes 6 & 7 of FIG. 4, where the optimized turn in combination with the wild-type α-helix 0 (SEQ ID NO: 24), does not confer high solubility. Only the presence of the α-helix0 mutations, either with or without the optimized turn sequence (see FIG. 4 lanes 4 & 5 and lanes 8 & 9, respectively), allows high levels of fusion protease in the supernatant fractions.

However, the experiment shown in FIG. 4 only shows whether the expressed protein fractionates in the soluble fraction. A more detailed analysis of the construct's suitability for structural studies was preformed using NMR, where the protein aggregation state could be assessed. $^{1}H$-$^{15}N$ HSQC NMR spectra were collected for $^{15}N$-labeled proteins of SEQ ID NO: 12 and SEQ ID NO: 14. As shown in FIG. 5, the protein of SEQ ID NO: 14 (panel B—mutant α-helix 0 with optimized linker) generates a higher quality HSQC spectrum (as judged by NMR linewidth and resolution of 2D peaks) than the protein produced from SEQ ID NO: 12 (panel A—mutant α-helix 0 with non-optimized linker). This analysis shows that the optimized linker derived in Experiment 5 is contributing favorably to the overall solubility and non-aggregation of the modified HCV NS4a–NS3 fusion protease.

Example 6

Incorporation in Modified HCV NS4a–NS3 Fusion Proteases of Naturally-occurring Hydrophobic-to-hydrophilic Residue Substitutions and Change of Non-zinc-binding Cysteines to Non-cysteine Amino Acids Inspection of a protein sequence alignment of the HCV NS3 portions of different published HCV isolates (not shown) showed that many residue positions are variable among the different isolates. In particular, a number of solvent-exposed surface residue positions can take on a number of different naturally-occurring amino-acid residue types that differ in their hydrophobic-hydrophlilic character. These residues include $Ala_{39}$ (sometimes Ser), $Ala_{40}$ (sometimes Thr), $Pro_{67}$ (sometimes Ser), $Ile_{72}$ (sometimes Thr), and $Pro_{86}$ (sometimes Gln).

Substitution of non-essential cysteine residues is a method sometimes utilized in attempts to improve a protein's biochemical properties by reducing the tendancy of the protein to form disulfide-linked multimers upon oxidation (for example, Yamazaki et al., *Protein Science* [1996]5, 495–506). Preliminiary experiments showed that substitution of each of the four non-zinc-binding cysteines within HCV NS3 protease had minimal effects upon enzymatic activity (data not shown). Inspection of the protein sequence alignment showed that, within the a given sequence, two of the non-zinc-binding cysteine residues ($Cys_{47}$ and $Cys_{52}$) either appeared together as a cysteine pair or were both changed to non-cysteine residue types (coupled with their spatial arrangement within the HCV NS3 protease sequence, this fact indicates that this pair is likely to form a disulfide linkage). A third non-zinc-binding cysteine residue ($Cys_{159}$), was also targeted for mutagenesis (although this position is invariant among the different HCV isolates inspected).

Using this information, six oligonucleotides were designed that code for alternate residue types at selected solvent-exposed residue positions, with a bias toward substitution of hydrophilic residue-types in place of hydrophobic ones. In addition, three of the four non-zinc-binding cysteine residues ($Cys_{47}$, $Cys_{52}$, and $Cys_{159}$) were changed to non-cysteine residues.

Surface Oligo#1 (P86Q):

5'-ACGGGAACCCTGCGGAGCTGCCAAC-
CAACCAGGTCTTTG-3'

Surface Oligo#2 (P67P/S; I72Q):

5'-CAACGTTGGTGTACATCTGGGTAACCG-
GACCTTTCGRGGAAGCGATGGTACGGGT-3'

Surface Oligo#3 (A39A/S; A40T);

5'-CCAGGAAGGTCTGGGTAGMGGTGGAAACGATCTGAAC-
3'

Cys Oligo#1 (C159S/T);

5'-CTTTAGCAACACCACGGGTGGWAACAG-
CAGCACGGAAGAT-3'

Cys Oligo#2 (C47S/T; C52L/M);

5'-ACCGTGGTAAACGGTCCACAKAACAC-
CGTTGATGGWGGTAGCCAGGAAGGTC-3'

Cys Oligo#3 (A39A/S; A40T; C47S/T; C52L/M);

5'-ACCGTGGTAAACGGTCCACAKAACAC-
CGTTGATGGWGGTAGCCAGGAAG-
GTCTGGGTAGMGGTGGAAACGATCTGAAC-3

Where W=(A,T); K=(G,T); M=(A,C); R=(A,G).

The site-directed mutations were introduced into SEQ ID NO:13 by the dutung method (Kunkle, 1985) using the Muta-Gene Phagemid kit (BioRad). The mutations were generated by using the six oligonucleotides in different combinations to produce distinct sets of clones having different mutation combinations. Expression levels and solubilities of the randomly-picked mutant NS4a–NS3 fusion protease variants were monitored by SDS-PAGE analysis of the soluble fractions of induced cell lysates (similar to the analysis shown in FIG. 4) and some of the clones exhibiting enhanced protease solubilty were sequenced. The A40T, I72T, P86Q mutations were found to have the most pronounced positive effect on solubility.

To combine these mutations with the optimized linker sequence generated in Example 5, DNA sequences encoding the A40T, I72T, P86Q surface mutants were subdloned into SEQ ID NO: 15 without and with the C47S, C52L, and C159S cysteine mutants to produce the proteins presented in SEQ ID NO: 16 (FIG. 14) and SEQ ID NO: 18 (see FIG. 15), respectively. The 2D $^{1}H$-$^{15}N$ HSQC NMR spectrum of protein produced from SEQ ID NO: 18 shown in FIG. 5 panel C clearly indicates that this protease variant is highly non-aggregating and suitable for high-resolution NMR structural analysis. *E. coli* cells harboring the plasmid containing SEQ ID NO: 19, which is the DNA sequence encoding SEQ ID NO: 18, have been deposited with the ATCC and have ATCC accession number 207040.

Additional modified HCV NS4a–NS3 fusion proteases analogous to the one shown in SEQ ID NO: 18 were constructed in which another α-helix 0 variant sequence identified in Example 4 was substituted. Variant α-Helix 0–7, identified as SEQ ID NO: 9 in FIG. 11, was substituted, resulting in SEQ ID NO: 20 (see FIG. 16) and SEQ ID NO: 22 (see FIG. 17). SEQ ID NO: 22 is the same as SEQ ID NO: 20, except that an additional naturally-occurring amino-acid substitution (C16T) was included. When expressed, both of these modified HCV NS4a–NS3 fusion proteases had solubilities comparable to that of SEQ ID NO: 18 and, as expected, exhibited chromatographic properties on ion exchange media that differed somewhat from the SEQ ID NO: 18 homolog. 2D $^1$H-$^{15}$N HSQC spectra confirmed that these protein variants were similarly folded to that of the SEQ ID NO: 18 protease (data not shown). *E. coli* cells harboring the plasmid containing SEQ ID NO: 23, which is the DNA sequence encoding SEQ ID NO: 22, have been deposited with the ATCC and have ATCC accession number 207041.

Example 7

Expression and Purification in*E. coli*

All constricts were expressed in *E. coli* strain BL21(DE3) (Novagen) using one of the pET plasmid vectors (Novogen). Proteins were expressed either as polyhistidine-tagged proteins using the pET28a vector, or as non-tagged proteins using the pET29a vector. Probably due to optimized bacterial codon usage and massive overproduction, expression of these constructs resulted in translational readthrough protein products (~10–20%), in addition to the predicted full-length protein product. Modification of the expression vectors to include a triple-stop set of codons (TAA TAA TGA) results in the elimination of the readthrough products (data not shown).

The following two purification methods are outlined for the modified HCV NS4a–NS3 fusion protease produced from expression of SEQ ID NO: 19 in the pET29a vector system (no tag). However, one skilled in the art could readily modify the procedures slightly to purify any of the modified forms of HCV NS3 protease of the present invention.

Method 1

Expression of non-tagged variant expressed from SEQ ID NO: 19 was carried out in minimal bacterial growth media with induction with 0.3 mM IPTG when the cell density reached OD600=1.0. Concurrent with induction of the culture, ZnCl$_2$ was added to final 30 µM concentration and the cells were transferred to 20 degrees C for 20 hours.

After centrifugation, the cell pellet was resuspended in 25 mM Na—phosphate buffer pH 7.5, 0.5 M NaCl, 2 mM DTT, 10 µM ZnCl$_2$ and cells were disrupted by passage through a High Pressure Homogenizer (RANNI model 8.30H). The homogenate was clarified at 15,000 (Sorvall model SS34 rotor) rpm for 30 min and 10 mM MgCl2, and 20 µg/ml DNAse/RNAse were added to the supernatant.

After incubation at room temperature for 10 minutes, the supernatant was diluted twice with 25 mM Na—phosphate buffer, 2 mM DTT, 10 µM ZnCl$_2$ and applied onto Macro-Prep S column (Bio-Rad, 1 kg of resin) equilibrated with 25 mM Na—phosphate pH 7.5, 0.2 M NaCl, 2 mM DTT, 10 µM ZnCl$_2$. After washing the column till OD280~0.1, the bound protein was eluted with the same buffer with 0.5 M NaCl.

The eluate was concentration on an Amicon YM5 membrane and applied onto a Superdex 30 26/60 column equilibrated with 25 mM Na—phosphate pH-7.5, 0.2 M NaCl, 2 mM DTT, 10µM ZnCl$_2$. The fractions of the NS3 peak were applied onto SP Sepharose 26/10. Buffer A was the same buffer as for the Superdex 30 column. Buffer B is the same buffer with 1 M NaCl. The protein peak elutes at 0.5–0.6 M NaCl.

For crystallization, the purified protein was exchanged into 0.5 M NaCl, 25 mM MES (2-(N-Morpholino) ethanesulfonic Acid), pH 6.5, 10% (v/v) glycerol, 2 mM dithiothreitol (DTT) and could be concentrated to 5 mM (~100 mg/ml). For NMR spectroscopy, the protein was exchanged into 25 mM sodium phosphate pH 6.5, 50 mM sodium sulfate, 2 mM deuterated DTT, and 10% D$_2$O and could be concentrated to at least 3 mM.

Integrity of the preparation was verified by mass spec analysis. Using this purification method, the final yields are typically 50–65 mg pure protein per liter culture.

Method 2

For protein for crystallography, the following modified protocol was found to produce a preparation that crystallized readily (overnight):

After cell disruption in the homogenizer (as in Method 1), the homogenate was centrifuged (Sorvall model SS34) for 30 min at 16,000 rpm. The supernatant was treated with PEI (polyethylenimine—0.2% final) for 20 min at room temperature upon stirring. The white solution was centrifuged at 16,000 rpm for 20 min and supernatant was precipitated with ammonium sulfate (40%) at 4 degrees C for 30 min. The solution was centrifuged at 10,000 rpm for 30 min. The pellet was resuspended in 25 mM Na—phosphate, pH 7.5, 2 mM DTT, 10:M ZnCl$_2$ (10 ml per liter of culture) and centrifuged again at 16,000 rpm for 10 min. The supernatant was applied first onto Superdex 75 26/60 column equilibrated with 25 mM Na—Phosphate buffer, pH 7.5, 0.2 M NaCl, 2 mM DTT, 10:M ZnCl$_2$. The peak fractions were applied then to an SP Sepharose 26/10 column. Buffers A and B are the same as in Method 1. After concentration of peak functions on Amicon membrane, the protein was applied onto Superdex 30 16/60 equilibrated with 25 mM Na—phosphate, pH 7.5, 2 mM DTT, 10:M ZnCl$_2$ and no salt. Only the purest side fractions of HCV NS3 protease were collected and pooled.

After concentration (Millipore Ultrafree-5K cutoff), the protein was exchanged into 25 mM MES buffer, pH 6.5, 0.5 M NaCl, 2 mM DTT, 10:M ZnCl$_2$. The protein preparation concentrated easily and readily produced crystals (as outlined in Example 10) even after four months of storage at 4 degrees C.

Example 8

NMR Spectroscopy of Modified HCV NS4a–NS3 Fusion Proteases

Modified HCV NS4a–NS3 fusion proteases were prepared for NMR analysis by exchanging the purified protein (see Method 1, Example 7) into NMR buffer (25 mM sodium phosphate pH 6.5, 50 mM sodium sulfate, 2 mM deuterated DTT, and 10% D20). Protease samples both with and without readthrough product (see Example 7) were successfully used for NMR spectroscopy in both Examples 8 and 9. Sample concentrations ranged from 0.2 mM to 3 mM.

Two-dimensional $^1$H-$^{15}$N HSQC NMR spectra were obtained using a WATERGATE HSQC pulse sequence (Mori et al., (1995), *J Magin. Reson*. B108, 94–98; Sklenar, (1995) *J Magn. Res*. A114, 132–135) on a Varian UNITY PLUS 600 MHz NMR spectrometer. The data were collected at 30 degrees C with 4 transients per FID and either 128 or 256 increments, with spectral widths of 10.0 and 2.4 kHz in $F_2(^1H)$ and $F_1(^{15}N)$, respectively.

A 1.5 mM solutions of a double-labeled ($^{13}$C-$^{15}$N) preparation of apo-HCV protease (SEQ ID NO: 18) was prepared. A full set of NMR spectra were collected and used to determine the backbone NMR resonances of the apo-HCV protease. The 3D NMR experiments included HNCO, HNCACO, HNCACB, CBCACONH, HBHACONH, HNCAHA, HCCH-TOCSY, $^{15}$N-edited NOESY and $^{13}$C-edited NOESY (see Clore and Gronenbom, *Meth. Enzymol*. 239, 349–363 (1994) for references to these experiments).

Backbone NMR resonances for 155 of the 187 non-proline residues and 8 of the 11 proline residues were obtained along with most of the sidechain assignments. These assignments include the catalytic triad residues $His_{57}$, $Asp_{81}$, and $Ser_{139}$ and the residues spatially near to them, indicating that the apo-form of the protein is a good reagent for NMR analysis of protease:inhibitor complexes Example 9

NMR of a Complex of a Modified HCV NS4a–NS3 Fusion Protease with an Inhibitor

Figure 7:
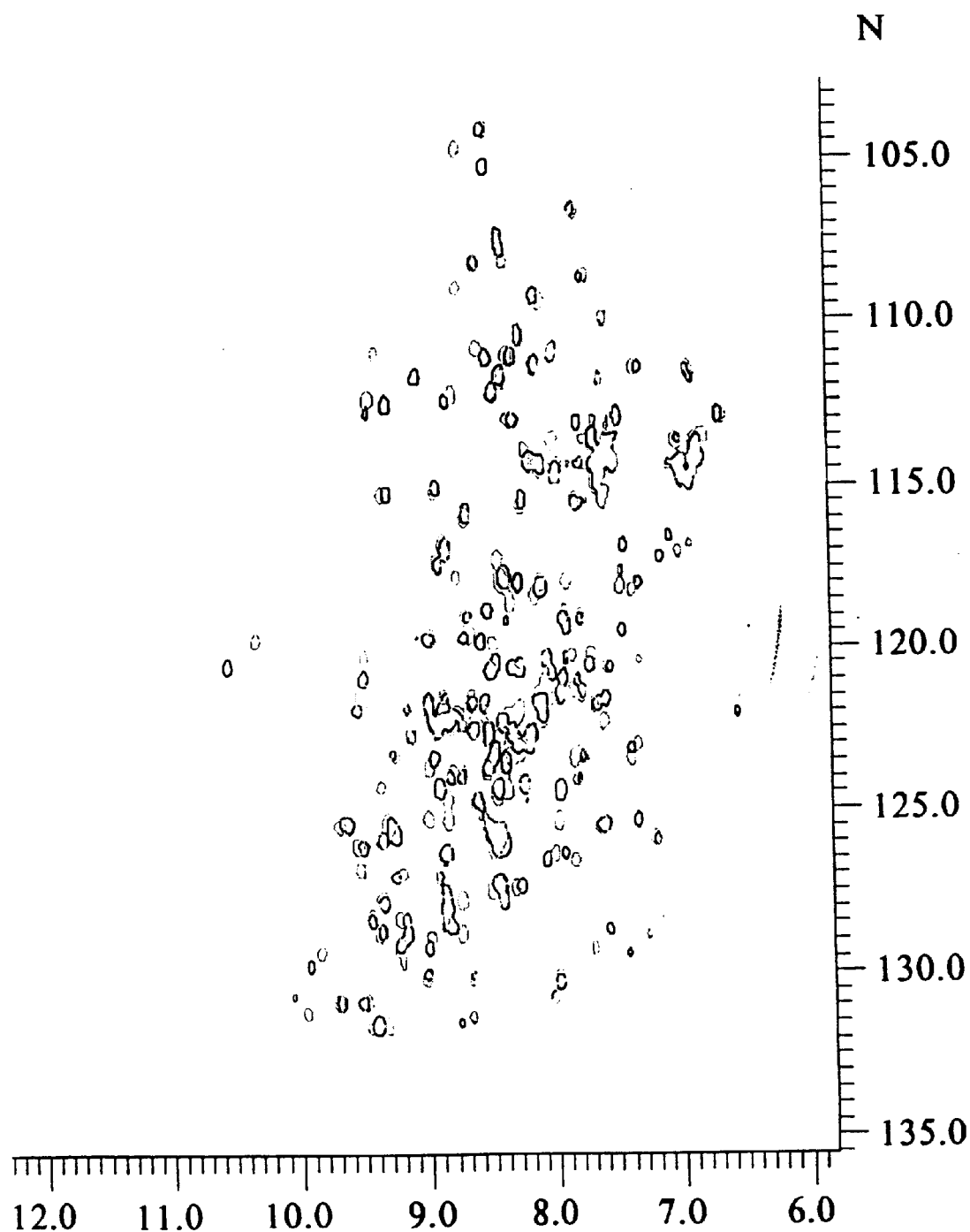
FIG. 7. Overlayed NMR $^1$H-$^{15}$N NHSQC spectra of a modified HCV NS4a–NS3 fusion protease with optimized linker (SEQ ID NO: 18) in apo-form and complexed with a peptide inhibitor (see Example 9). Apo-protease (thin grey line), peptide-complexed protease (thick black line).

A complex between a $^{15}N$-labeled HCV NS4a–NS3 fusion protease (SEQ ID NO: 18) and an inhibitor peptide (Ac-Asp-D-Glu-Leu-Ile-Cha-Cys-OH) (Ingallinella et al., Biochemistry 37, 8906–8914 (1998)) was formed by forming a 1:1 complex of the two components (at 200 µM concentration) in the NMR buffer described in Example 8. A 2D HSQC spectrum was collected. The HSQC spectra of the apo- and peptide-complexed soluble modified HCV NS4a–NS3 fusion protease (SEQ ID NO: 18) are overlayed in FIG. 7. Many residues undergo chemical shift perturbations upon addition of the inhibitor, including the active site residues.

Example 10

Crystal Structure of a Complex of Modified HCV NS4a–NS3 Fusion Protease with an Inhibitor The modified HCV NS4a–NS3 fusion protease produced by Method 2 in Example 7 is well suited to support X-ray crystallographic studies. In this Example, the protein preparations included 10–20% translational readthrough product (see Example 7). The preparations produced crystals of a complex with inhibitor overnight and a structure of the complex with inhibitor to 2.1 Å resolution.

Crystals of the soluble modified HCV NS4a–NS3 fusion protease complexed with peptidic inhibitor Ac-Asp-D-Glu-Leu-Ile-Cha-Cys-OH [$IC_{50}$=15 nM, Ingallinella et al., Biochemistry 37, 8906–8914 (1998)] were grown by standard hanging-drop vapor-diffusion methods at room temperature. Protein solution: 21.6 mg/ml protein in 0.5 M NaCl, 25 mM MES, pH 6.5, 10% (v/v) glycerol, 2 mM DTT, and 5.64 mM inhibitor (6X molar excess) incubated at room temperature for 2 hours. Reservoir solution: 2 M ammonium sulfate, 0.1 M sodium acetate, pH 4.6, 1% (v/v) PEG monomethyl ester 350, 5 mM zinc chloride. Droplets were composed of equal-volume aliquots of protein and reservoir solutions. Crystals were obtained overnight by these conditions.

A crystal was taken from its droplet and placed in a small volume of reservoir solution that had been made 20% (v/v) in glycerol. It was extracted with a standard Hampton fiber loop mounted in a Hampton pin and immediately introduced into the 100 K nitrogen stream from an Oxford Cryosystems low-temperature device.

Data to 2 Å resolution were collected from this crystal on a rotating-anode source (CuK()) with an R-AXIS II detector. Completeness is 94% from 20–2 Å resolution, and 64% in the outer shell (2.07–2.00 Å), with R(symm)s of 9.1% and 39.7% for all and for outer shell, respectively.

X-ray diffraction from this crystal indicates space group $P4_12_12$ with unit cell parameters a=b=67.1, c=81.2 Å and one molecule per asymmetric unit.

The structure was solved by application of standard molecular-replacement techniques with a NS4a–NS3 fusion search model based upon a previously reported structure of HCV protease:NS4a complex whose coordinates are on deposit with the Protein Data Bank [1JXP.pdb as described in Protein Sci. 7, 837–847 (1998)]. Refinement of the structure by XPLOR with data from 20.0–2.1 Å resolution and F/((F)>1.0 was suspended at an R-factor of 19.7% and R-free of 27.6%. The current model (1) includes about 120 water molecules, of which about 2/3 were added by an automated routine and have not been checked in the electron density map, (2) lacks modeled residues for loops at 0–4 and 87–89 for which density is not clear, and (3) includes no alternate conformations for side chains although several were found.

Electron density for the entire inhibitor is clearly seen, and its conformation and that of its binding site on the protein are unambiguously defined, thus making the structure immediately useful for drug design purposes. The quality of the inhibitor map can be seen in FIG. 8. The inhibitor binds entirely on the P side of the active site and the carboxylate at its C-terminus binds in a pocket that corresponds to the oxyanion hole of the classical serine protease active site. Away from the active site, a zinc ion is coordinated by the side chains of cysteines at 97, 99, and 145, and by a water molecule, although the identity of this latter ligand is questioned. As the B factor of this water refines to 2 $Å^2$ and there is a large residual peak in the difference map at its position, it is suspected of being another component of the crystallization fluid and we have refined it as a chloride ion.

The above examples are illustrative and do not limit the claims.

LITERATURE CITATIONS

1. Choo, Q.-L., Kuo, G., Weiner, A. J., Bradley, L. R. D. W. and Houghton, M. (1989). Science 244, 359–362.
2. Kuo, G., Choo, W.-L., Alter, H. J., Gitnick, G. L., Redeker, A. G., Purcell, R. H., Miyamura, T., Dienstag, J. L., Alter, M. J., Stevens, C. E., Tegtmeier, G. E., Bonino, F., Colombo, M., Lee, W.-S., Kuo, C., Berger, K., Shuster, J. R., Overby, L. R., Bradley, D. W. and Houghton, M. (1989). Science 244, 362–364.
3. Choo, Q.-L., Richman, K. H., Han, J. H., Berger, K., Lee, C., Dong, C., Gallegos, C., Coit, D., Medina-Selby, A., Barr, P. J., Weiner, A. J., Bradley, D. W., Kuo, G. and Houghton, M. (1991). Procedings of the National Academy of Sciences USA 88, 2451–2455.
4. Grakoui, A., McCourt, D. W., Wychowski, C., Feinstone, S. M. and Rice C. M. (1993a). Journal of Virology 67, 2832–2843.
5. Bartenschlager, R., Ahlborn-Laake, L., Mous, J. & Jacobsen, H. (1993). Journal of Virology 67, 3835–3844.
6. Grakoui, A., Wychowski, C., Lin, C., Feinstone, S. M. and Rice C. M. (1993b). Journal of Virology 67, 1385–1395.
7. Hijikata, M., Mizushima, H., Akagi, T., Mori, S., Kakiuchi, N., Kato, N., Tanaka, T., Kimura, K. and Shimotohno, K. (1993a). Journal of Virology 67, 4665–4675.
8. Hijikata, M., Mizushima, H., Tanji, Y., Komada, Y., Hirowatari, Y., Akagi, T., Kato, N., Kimura, K., and Shimotohno, K. (1993b). Procedings of the National Academy of Sciences USA 90, 10773–10777.
9. Tomei, L., Failla, C., Santolini, E., De Francesco, R. and La Monica, N. (1993). Journal of Virology 67, 4017–4026.
10. Bartenschlager, R., Ahlbom-Laake, L., Mous, J. and Jacobsen, H. (1994). Journal of Virology 68, 5045–5055.
11. Eckart, M. R., Selby, M, Masiarz, F., Lee, C., Berger, K., Crawford, K., Kuo, C., Kuo, G., Houghton, M. and Choo, Q.-L. (1993). Biochemical and Biophysical Research Communications 192, 399–406.

12. Lin, C., Pragai, B., Grakoui, A., Xu, J. and Rice, C. (1994). Journal of Virology 68, 8147–8157.
13. Manabe, S., Fuke, I., Tanishita, O., Kaji, C., Gomi, Y., Yoshida, S., Mori, C., Takamizawa, A., Yosida, I. and Okayama, H. (1994). Virologty 198, 636–644.
14. Chambers, T. J., Weir, R. C., Grakoui, A., McCourt, D. W., Bazan, J. F., Fletterick, R. J. and Rice, C. M. (1990). Proceedings of the National Academy of Sciences, USA 87, 8898–8902.
15. Xu, J., Mendez, E., Caron, P. R., Lin, C., Murcko, M., Collet, M. S. and Rice, C. M. (1997). Journal of Virology 71, 5312–5322.
16. Overton, H., McMillan, D., Gillespie, F. and Mills, J. (1994). Journal of General Virology 76, 3009–3019.
17. Bartenschlager, R., Lohmann, V., Wilkinson, T. and Koch, J. 0. (1995) Journal of Virology 69, 7519–7528.
18. Bouffard, P., Bartenschlager, R., Ahlborn-Laake, L., Mous, J., Roberts, N. and Jacobsen, H. (1995) Virology 209, 52–59
19. Tanji, Y., Hijikata, M., Satoh, S., Kaneko, T. and Shimotono, K. (1995). Journal of Virology 69, 1575–1581.
20. Lin, C. and Rice, C. M. (1995). Proceedings of the National Academy of Sciences 92, 7622–7626.
21. Satoh, S., Tanji, Y., Hijikata, M., Kimura, K. and Shimotono, K. (1995). Journal of Virology 69, 4255–4260
22. Tanji, Y., Hijikata, M., Hirowatari, Y. and Shmotohno, K. (1994). Gene 145, 215–219.
23. Failla, C., Tomei, L., and De Francesco, R. (1995). Journal of Virology 69, 1769–1777.
24. Shoji, I., Suzuki, T., Chieda, S., Sato, M., Harada, T., Chiba, T., Matsuura, Y. and Miyamura, T. (1995). Hepatology 22, 1648–1655.
25. Jin, L. and Peterson, D. L. (1995). Archives of Biochemistry and Biophysics 323, 47–53.
26. Lin, C., Thomson, J. A., and Rice, C. M. (1995) Journal of Virology 69, 4373–4380.
27. Tomei, L., Failla, C., Vitale, R. L., Bianchi, E. and De Francesco, R. (1995). Journal of General Virology 77, 1065–1070.
28. Shimizu, Y., Yamaji, K., Masuho, Y. Yokota, T., Inoue, H., Sudo, K., Satoh, S. and Shimotohno, K. (1996). Journal of Virology 70, 127–132.
29. Lin, C. and Rice, C. M. (1995). Proceedings of the National Academy of Sciences USA 92, 7622–7626.
30. Kim, J. L., Morgenstern, Lin, C., Fox, T., Dwyer, M. D., Landro, J. A., Chambers, S. P., Markland, W., Lepre, C. A., O'Malley, E. T., Harbeson, S. L., Rice, C. M., Murcko, M. A., Caron, P. R., and Thomson, J. A. (1996). Cell 87, 343–355.
31. Love, R. A., Parge, H. E., Wickersham, J. A., Hostomsky, Z., Habuka, N., Moomaw, E. W., Adachi, T., and Hostomask, Z. (1996) Cell 87, 331–342.
32. Yan, Y., Li, Y., Munshi, S., Sardana, V., Cole, J., Sardana, M., Steinkuehler, C., Tomei, L., De Francesco, R., Kuo, L. C., and Chen, Z. (1998). Protein Science 7, 837–847.
33. De Francesco, R., Urbani, A., Nardi, M. C., Tomei, L., Steinkuehler, C., and Tramontano, A. (1996). Biochemistry 35, 13282–13287.
34. Suzuki, T., Sato, M., Chieda, S., Shoji, I., Harada, T., Yamakawa, Y., Watabe, S., Matsuura, Y. and Miyamura, Tatsuo (1995). Journal of General Virology 76, 3021–3029.
35. Hong, Z., Ferrari, E., Wright-Minogue, J., Chase, R., Risano, C., Seelig, G., Lee, C-G and Kwong, A. D. (1996). Journal of Virology 70,4261–4268.
36. Steinkuhler, C., Urbani, A., Tomei, L., Biasiol, G., Sardana, M., Bianchi, E., Pessi, A. and De Francesco, R. (1996). Journal of Virology 70, 6694–6700.
37. Inoue, H., Sakashita, Shimizu, Y., Yamaji, K., Yokota, T., Sudo, K., Shigeta, S. and Shimotohno, K. (1998). Biochemical and Biophysical Research Communications 245, 478–482.
38. Taremi, S. S., Beyer, B., Maher, M., Yao, N., Prosise, W., Weber, P. C. and Malcolm, B. A. (1998). Protein Science 7, 2143–2149.
39. Kunkel, T. A.(1985) Proc. Natl. Acad. Sci. USA, 82, 488
40. Taliani, M., Bianchi, E., Narjes, F., Fossatelli, M., Urbani, A., Steinkuhler, C., De Francesco, R. and Pessi, A. (1996). Analytical Biochemistry 240,. 60–67
41. Pasquo, A., Nardi, M. D., Dismasi, N., Tomei, L., Steinkuhler, C., Delmastro, P., and DeFrancesco, R. (1996) Folding and Design 3, 433–441

What is claimed is:

1. A modified HCV NS3 protease comprising at least one substitution in HCV NS3 protease of a hydrophobic α-helix 0 amino acid residue to a hydrophilic amino acid residue wherein said modified HCV NS3 protease exhibits protease activity.

2. A modified HCV NS3 protease of claim 1 wherein said at least one substitution is of a hydrophobic β-helix 0 amino acid residue selected from the group consisting of $Leu_{13}$, $Leu_{14}$, $Ile_{17}$, $Ile_{18}$, and $Leu_{21}$ wherein $Leu_{13}$, $Leu_{14}$, $Ile_{17}$, $Ile_{18}$, and $Leu_{21}$ correspond respectively to residues 14, 15, 18, 19, and 22 of SEQ ID NO:1.

3. The modified HCV NS3 protease of claim 2 comprising at least one substitution selected from the group consisting of: $Leu_{13}$ is substituted to Glu, $Leu_{14}$ is substituted to Glu, $Ile_{17}$ is substituted to Gln, $Ile_{18}$ is substituted to Glu, and $Leu_{21}$ is substituted to Gln.

4. The modified HCV NS3 protease of claim 2 comprising at least one substitution selected from the group consisting of $Leu_{13}$ is substituted to Glu, $Leu_{14}$ is substituted to Gln, $Ile_{17}$ is substituted to Gln, $Ile_{18}$ is substituted to Lys, and $Leu_{21}$, is substituted to His.

5. The modified HCV NS3 protease of claim 2 comprising at least one substitution selected from the group consisting of $Leu_{13}$ is substituted to Glu, $Leu_{14}$ is substituted to Glu, $Ile_{17}$ is substituted to Glu, $Ile_{18}$ is substituted to Gln, and $Leu_{21}$, is substituted to Glu.

6. The modified HCV NS3 protease of claim 2 comprising at least one substitution selected from the group consisting of $Leu_{13}$ is substituted to Asn, $Leu_{14}$ is substituted to Gln, $Ile_{17}$ is substituted to Glu, $Ile_{18}$ is substituted to Lys, and $Leu_{21}$ is substituted to Glu.

7. The modified HCV NS3 protease of claim 2 comprising at least one substitution selected from the group consisting of $Leu_{13}$ is substituted to Glu, $Leu_{14}$ is substituted to Gln, $Ile_{17}$ is substituted to Asp, $Ile_{18}$ is substituted to Glu, and $Leu_{21}$ is substituted to Glu.

8. The modified HCV NS3 protease of claim 2 comprising at least one substitution selected from the group consisting of $Leu_{13}$ is substituted to Glu, $Leu_{14}$ is substituted to Glu, $Ile_{17}$ is substituted to Glu, $Ile_{18}$ is substituted to Gln, and $Leu_{21}$ is substituted to Glu.

9. The modified HCV NS3 protease of claim 2 wherein $Leu_{13}$, $Leu_{14}$, $Ile_{17}$, $Ile_{18}$, and $Leu_{21}$ are substituted to hydrophilic amino acid residues.

10. The modified HCV NS3 protease of claim 1 wherein said HCV NS3 protease comprises residues 1–181 of the amino acid sequence of HCV NS3 as shown in SEQ ID NO: 1 or comprises a portion of wild type HCV NS3 that confers Drotease activity and that differs from residues 1–181 of the amino acid sequence of HCV NS3 as shown in SEQ ID NO: 1 by the inclusion or deletion of residues at either the N- or C- terminus.

11. The modified HCV NS3 protease of claim 10 wherein said HCV NS3 protease comprises residues 1–181 of the amino acid sequence of HCV NS3 as shown in SEQ ID NO: 1.

12. The modified HCV NS3 protease of claim 1 further comprising at least one substitution of a hydrophobic amino acid residue not in the α-helix 0 to a hydrophilic amino acid residue.

13. The modified HCV NS3 protease of claim 1 further comprising at least one substitution of a non-zinc-binding cysteine residue to a non-cysteine amino acid residue.

14. A modified HCV NS4a–NS3 fusion protease comprising the modified HCV NS3 protease of claim 1 fused to a HCV NS4a or a modified HCV NS4a wherein said modified HCV NS4a comprises residues 21–31 of full length HCV NS4a as shown in SEQ. ID. NO 26 having NS4a residue substituted to Asn.

15. The modified HCV NS4a–NS3 fusion protease of claim 14 wherein said HCV NS4a comprises residues 21–31 of full-length HV NS4a as shown in SEQ ID NO: 26.

16. The modified HCV NS4a–NS3 fusion protease of claim 14 further comprising a linker.

17. The modified HCV NS4a–NS3 fusion protease of claim 16 wherein the linker comprises an optimized linker sequence.

18. The modified HCV NS4a–NS3 fusion protease of claim 17 wherein the optimized linker sequence is Ser-Gly- Asp-Thr where Ser corresponds to HCV NS4a residue $Ser_{32}$ and Thr corresponds to HCV NS3 residue $Thr_4$ wherein Ser-Gly-Asp-Thr are shown in residues 16–19 of SEQ. ID. NO. 18.

19. The modified HCV NS4a–NS3 fusion protease of claim 14 wherein the HCV NS4a or modified HCV NS4a is linked to the amino terminus of the modified HCV NS3 protease.

20. A modified HCV NS4a–NS3 fusion protease of claim 14 comprising an amino acid sequence selected from the group consisting of: SEQ ID NO: 12, SEQ ID NO: 14, SEQ ID NO: 16, SEQ ID NO: 18, SEQ ID NO: 20, and SEQ ID NO: 22.

21. The modified HCV NS4a–NS3 protease of claim 14 encoded by the nucleic acid molecule deposited in ATCC as 207040.

22. A modified HCV NS4a–NS3 protease of claim 14 encoded by the nucleic acid molecule deposited in ATCC as 207041.

23. The modified HCV NS3 protease of claim 1 wherein said HCV NS3 protease comprises residues 2–182 of the amino acid sequence shown in SEQ ID NO: 1 or comprises a portion of wild type HCV NS3 that confers protease activity and that differs from residues 2–182 of the amino acid sequence as shown in SEQ ID NO: 1 by the inclusion or deletion of residues at either the N- or C-terminus.

24. A modified HCV NS4a-NS3 fusion protease comprising a modified HCV NS3 protease of claim 23 fused to HCV NS4a or a modified HCV NS4a, wherein said modified HCV NS4a comprises residues 21–31 of full length HCV NS4a as shown in SEQ ID NO:26 having NS4a residue 30 substituted to Asn.

25. The modified HCV NS3 protease of claim 1 wherein said HCV NS3 protease comprises residues 2–182 of the amino acid sequence shown in SEQ ID NO: 1.

26. A modified HCV NS4a-HS3 fusion protease comprising a modified HCV NS3 protease of claim 25 fused to a HCV NS4a or a modified HCV NS4a, wherein said modified HCV NS4a comprises residues 21–31 of full length HCV NS4a as shown in SEQ ID NO:26 having NS4a residue 30 substituted to Asn.

* * * * *

UNITED STATES PATENT AND TRADEMARK OFFICE
CERTIFICATE OF CORRECTION

PATENT NO. : 6,333,186 B1 Page 1 of 1
DATED : December 25, 2001
INVENTOR(S) : Wittekind et al.

It is certified that error appears in the above-identified patent and that said Letters Patent is hereby corrected as shown below:

Column 45,
Line 35, replace "β-helix" with -- α-helix --
Line 57, replace "Leul$_{14}$" with -- Leu$_{14}$ --

Column 46,
Line 56, after the word "residue" please add -- 30 --
Line 60, after the word "full-length" replace "HV" with -- HCV --

Column 47,
Line 17, replace "A modified" with -- The modified --

Signed and Sealed this

Fourth Day of February, 2003

JAMES E. ROGAN
*Director of the United States Patent and Trademark Office*

UNITED STATES PATENT AND TRADEMARK OFFICE
CERTIFICATE OF CORRECTION

| | | |
|---|---|---|
| PATENT NO. | : 6,333,186 B1 | Page 1 of 1 |
| APPLICATION NO. | : 09/478479 | |
| DATED | : December 25, 2001 | |
| INVENTOR(S) | : Goldfarb Valentina et al. | |

It is certified that error appears in the above-identified patent and that said Letters Patent is hereby corrected as shown below:

In claim 5, Col. 45, line 53, replace "Glu" with -- Gln --

In claim 10, Col. 46, line 37, replace "Drotease" with -- Protease --

Signed and Sealed this

First Day of August, 2006

JON W. DUDAS
*Director of the United States Patent and Trademark Office*